(12) United States Patent  (10) Patent No.: US 7,081,466 B2
Koya et al.                  (45) Date of Patent: *Jul. 25, 2006

(54) 2-AROYLIMIDAZOLE COMPOUNDS FOR TREATING CANCER

(75) Inventors: Keizo Koya, Brookline, MA (US); Lijun Sun, Harvard, MA (US); Mitsunori Ono, Lexington, MA (US); David James, Cambridge, MA (US); Weiwen Ying, Aver, MA (US); Shoujun Chen, Billerica, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 110 days.

This patent is subject to a terminal disclaimer.

(21) Appl. No.: 10/802,292

(22) Filed: Mar. 16, 2004

(65) Prior Publication Data

US 2004/0186129 A1    Sep. 23, 2004

Related U.S. Application Data

(63) Continuation of application No. 10/233,371, filed on Aug. 29, 2002, now Pat. No. 6,743,919.

(60) Provisional application No. 60/322,105, filed on Sep. 13, 2001.

(51) Int. Cl.
A61K 31/44 (2006.01)
A61K 31/445 (2006.01)
A61K 31/415 (2006.01)
C07D 471/02 (2006.01)
C07D 209/04 (2006.01)

(52) U.S. Cl. ............. 514/321; 514/300; 514/304; 514/299; 514/383; 514/387; 514/396; 546/118; 546/119; 546/121; 546/192; 546/197; 546/198; 548/469; 548/470

(58) Field of Classification Search ........... 546/118, 546/119, 121, 192, 197, 198; 548/469, 470; 514/321, 300, 304, 299, 383, 387, 396
See application file for complete search history.

(56) References Cited

U.S. PATENT DOCUMENTS 4,866,084 A    9/1989  Gunasekera et al.
(Continued)

FOREIGN PATENT DOCUMENTS

EP    0 272 810    6/1988
(Continued)

OTHER PUBLICATIONS

Achab, CA 125: 196083 (1996).
(Continued)

*Primary Examiner*—D. Margaret Seaman
(74) *Attorney, Agent, or Firm*—Hamilton, Brook, Smith & Reynolds, P.C.

(57) ABSTRACT

Disclosed is a compound represented by Structural Formula (I):

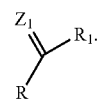

(I)

$R_1$ is a substituted or unsubstituted 2-imidazolyl group which is optionally fused to a substituted or unsubstituted aryl group.

$Z_1$ is $=O$, $=S$, $=NOR_{11}$.

R is represented by a Structural Formula selected from (II)–(VII):

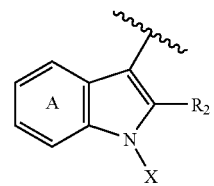

(II)

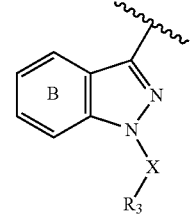

(III)

(IV)

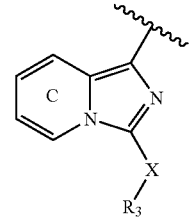

(V)

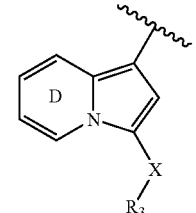

(VI)

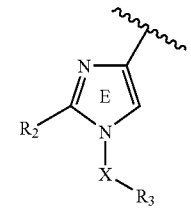

(VII)

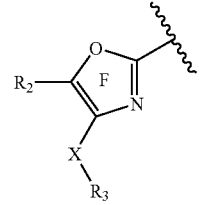

The variables in Structural Formulas (II)–(VII) are described herein.

33 Claims, 1 Drawing Sheet

U.S. PATENT DOCUMENTS

| | | | |
|---|---|---|---|
| 5,290,777 | A | 3/1994 | McConnell et al. |
| 5,464,835 | A | 11/1995 | McConnell et al. |
| 6,743,919 | B1 * | 6/2004 | Koya et al. .................. 546/118 |
| 2003/0096836 | A1 | 5/2003 | Koya et al. |

FOREIGN PATENT DOCUMENTS

| | | |
|---|---|---|
| EP | 0 272 810 A2 | 6/1988 |
| EP | 0 272 810 A3 | 6/1988 |
| WO | WO 97/12862 | 4/1997 |
| WO | WO 98/18466 | 5/1998 |
| WO | WO 99/42092 | 8/1999 |
| WO | WO 00/02857 | 1/2000 |
| WO | WO 00/071535 | 11/2000 |

OTHER PUBLICATIONS

Morris, CA 111: 4563, (1989).

Naef, CA 98: 88578, (1982).

Casapullo, A., et al., "New Bisindole Alkaloids of the Topsentin and Hamacanthin Classes from the Mediterranean Marine Sponge *RhapHisia lacazei*," *J. Nat. Prod.*, 63:447-451 (2000).

Naef, R., "Polarographic Properties and Electrochemical Reducation of 1,2-Dimethyl-3-indolyl Heteroaryl Ketones," *Helvetica Chimica Acta*, 65(6):1734-1742 (1982)—Nr.170.

Morris, S., et al., "Nitrogenous metabolites from the deep water sponge *Hexadella* sp.," *Canadian Journal of Chemistry* 67(4):677-681 (1989).

Achab, S., "A three-component approach to the marine bis-indole alkaloids: topsentin, deoxytopsentin and bromotopsentin," *Tetrahedron Letters* 37(31): 5503-5506 (1996).

* cited by examiner

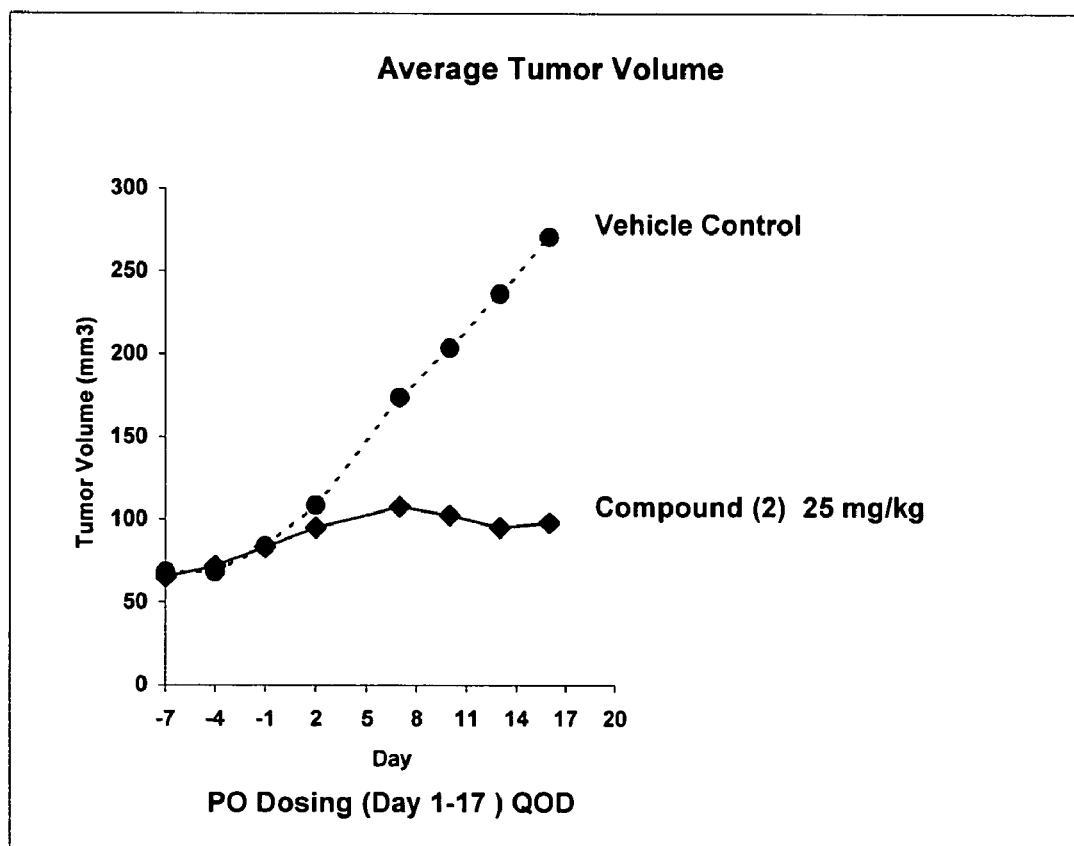

2-AROYLIMIDAZOLE COMPOUNDS FOR TREATING CANCER

RELATED APPLICATIONS

This application is a continuation of U.S. Application Ser. No. 10/233,371 (now U.S. Pat. No. 6,743,919 B2), filed Aug. 29, 2002, which claims the benefit of U.S. Provisional Application No. 60/322,105, filed on Sep. 13, 2001. The entire teachings of the above applications are incorporated herein by reference.

BACKGROUND OF THE INVENTION

Many methods are now available to be used in the treatment of cancer. Despite considerable advances, however, treatments for many cancers are inadequate for a number of reasons.

There are still cancers which simply do not respond or respond poorly to treatments currently available. Patients with treatable cancers must often undergo chemotherapy with drugs that cause severe side effects. Few of these drugs can be used orally. Perhaps the most serious problem associated with cancer chemotherapy is the development of multi-drug resistance by many tumors. For example, many tumors which initially respond positively to an anti-cancer therapy by decreasing in size or even going into remission often develop resistance to the drug. Tumors that have developed resistance to more than one drug are said to be "multi-drug resistant". There is little that can be done to halt or retard further progression of the disease, once a patient's cancer has become multi-drug resistant.

There is therefore still a need for new drugs which overcome one or more of the aforementioned shortcomings of drugs currently used in the treatment of cancer. Desirable properties of new anti-cancer drugs therefore include efficacy against tumors that are currently untreatable or poorly treatable, efficacy against multi-drug resistant tumors, oral bioavailability and/or reduced side effects.

SUMMARY OF THE INVENTION

It has now been found that certain 2-aroylimidazole compounds are cytotoxic against cancer cells, including multi-drug resistant cancer cells, from a number of different tissue types. For example, the IC$_{50}$ of Compounds (1)–(12) against the multi-drug resistant human cancer cell line MES-SA/DX5 and HL-60/TX1000 was less than 0.5 μM (see Examples 12–13 and 15). The structures of these compounds are shown in Example 11. In addition, the volume of tumors from the human breast cancer cell line MDA435 in nude mice was reduced by greater than 50% when Compound (2) was administered orally

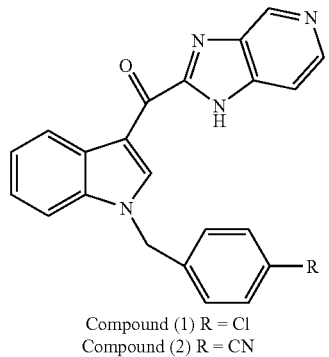

Compound (1) R = Cl
Compound (2) R = CN (Example 14). Little or no change in body weight was observed in mice treated with Compound (2), indicating that the compound caused minimal side-effects. Based on these results, novel 2-aroylimidazole compounds, pharmaceutical compositions comprising these 2-aroylimidazole compounds and methods of treating subjects with cancer by administering 2-aroylimidazole compounds are disclosed herein.

One embodiment of the present invention is a compound represented by Structural Formula (I):

$R_1$ is a substituted or unsubstituted 2-imidazolyl group which is optionally fused to a substituted or unsubstituted aryl group.

$Z_1$ is =O, =S, =NOR$_{11}$, or =NR$_{11}$.

R is represented by a Structural Formula selected from (II)–(VII):

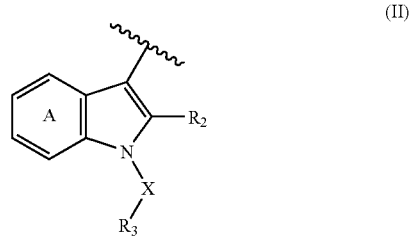

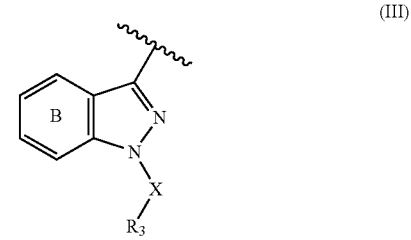

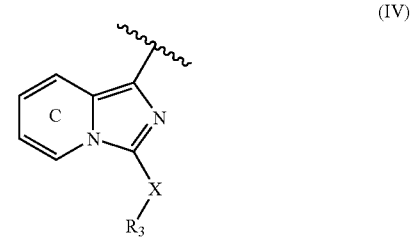

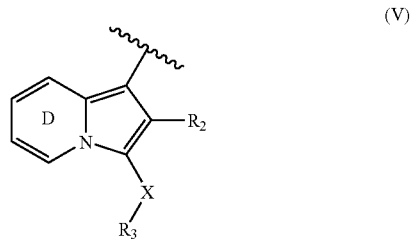

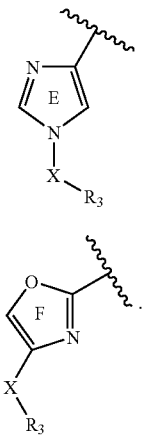

(VI)

(VII)

Preferably, R is represented by Structural Formula (II) or (V).

Rings A–F are independently substituted or unsubstituted and are optionally fused to an aryl group.

$R_2$ is —H, a substituted or unsubstituted alkyl group, or a substituted or unsubstituted aryl group.

$R_3$ is a substituted or unsubstituted aryl group or a substituted or unsubstituted aliphatic group.

X is a covalent bond, —C($R_4R_5$)—, —N($R_4$)—, —O—, —S—, —S(O)—, —S(O)$_2$—, —C(=O)—, —C(=O)—N($R_4$)— or —N($R_4$)—C(=O)—.

$R_4$ and $R_5$ are independently —H, an aliphatic group or a substituted aliphatic group.

$R_{11}$ is —H or a substituted or unsubstituted alkyl group.

In one aspect, when R is represented by Structural Formula (II), then X is not —S(O)— or —S(O)$_2$— and $R_3$ is not an aliphatic or substituted aliphatic group.

Another embodiment of the present invention is a pharmaceutical composition comprising a pharmaceutically acceptable carrier or diluent and a compound represented by Structural Formula (I). Preferably, the pharmaceutical composition comprises an effective amount of the compound. The pharmaceutical compositions can be used in therapy, e.g., as a treatment for cancer.

Another embodiment is a method of treating a subject with cancer. The method comprises administering to the subject an effective amount of a compound represented by Structural Formula (I).

Another embodiment is the use of a compound represented by Structural Formula (I) for the manufacture of a medicament for treating a subject with the cancer.

The disclosed compounds have many advantages when used to treat cancers. Most significantly, they are cytotoxic to many multi-drug resistant cell lines and therefore can be used when other traditional cancer chemotherapies have failed. In addition, they exhibit minimal side effects and are active when administered orally.

BRIEF DESCRIPTION OF THE FIGURE

The FIGURE is a graph depicting the anti-cancer effects of Compound (2) and a vehicle control administered orally to nude mice with human breast MDA435 tumors. The graph shows the volume of the tumors in mm$^3$ over time in days after the beginning of dosing with vehicle and 25 mg/kg of Compound (2) every second day.

DETAILED DESCRIPTION OF THE INVENTION

The disclosed invention is a compound represented by Structural Formula (I). The variables in Structural Formula (I) are as described above. Preferably, X is a covalent bond, —C($R_4R_5$)—, —N($R_4$)—, —O—C(=O)—, —C(=O)—N($R_4$)— or —N($R_4$)—C(=O)— and $R_3$ is a substituted or unsubstituted aryl group. More preferably, Rings A—F are a substituted or unsubstituted phenyl group; $R_2$ is —H; $R_3$ is a substituted or unsubstituted aryl group; X is —C($R_4R_5$)—, —N($R_4$)— or —O— (preferably —C($R_4R_5$)—); and $Z_1$ is =O. Even more preferalby, Rings A–F are a substituted or unsubstituted phenyl group; $R_2$ is —H; $R_3$ is a substituted or unsubstituted phenyl or pyridyl group; X is —C($R_4R_5$)—; $R_4$ and $R_5$ are both —H; and $Z_1$ is =O.

In one aspect, the 2-imidazoyl group designated by $R_1$ is represented by Structural Formula (VIII):

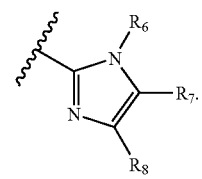

(VIII)

$R_6$–$R_8$ are independently —H or a substituent for an aryl group. Suitable substituents for an aryl group are described below. Preferably, $R_6$ and $R_7$ are both —H and $R_8$ is a substituent for an aryl group ring carbon.

In another aspect, the 2-imidazolyl group designated by $R_1$ is fused to an aromatic ring and is represented by Structural Formula (IX):

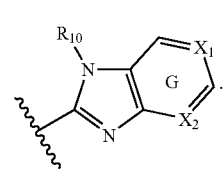

(IX)

$R_{10}$ is —H, an unsubstituted aliphatic group or a substituted aliphatic group, —C(O)—R$^g$, —S(O)$_2$R$^g$ or —S(O)$_2$—N(R$^g$)$_2$; $X_1$ and $X_2$ are independently —CH— or —N—; Ring G is substituted or unsubstituted; and each R$^g$ is —H or a substituted or unsubstituted aliphatic group. Preferably in Structural Formula (IX), $R_{10}$ is —H or a C1–C4 alkyl group; $X_1$ is —N—; $X_2$ is —CH—; and Ring G is substituted or unsubstituted.

In a preferred embodiment, the compound of the present invention is represented by Structural Formulas (X) or (XI):

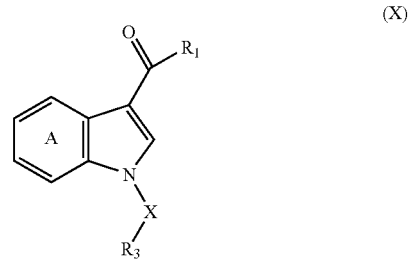

(X)

-continued

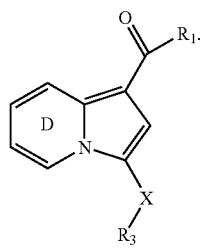
(XI)

In Structurla Formulas (X) and (XI), Rings A and D are substituted or unsubstituted; $R_1$ is represented by Structural Formulas (VIII) or (IX); X is —C($R_4R_5$)—, —O— or —N($R_4$)— (preferably —C($R_4R_5$)—); and $R_3$ is a substituted or unsubstituted phenyl or pyridyl group. More preferably, $R_1$ is represented by Structural Formula (VIII) or (IX), X is —CH$_2$—; $R_3$ is a substituted or unsubstituted phenyl or pyridyl group; $R_{10}$ is —H or a C1–C4 alkyl group; $X_1$ is —N—; $X_2$ is —CH—; and Ring G is unsubstituted.

The term "aryl group" refers to carbocyclic aromatic groups such as phenyl, naphthyl, and anthracyl, and heteroaryl groups such as imidazolyl, isoimidazolyl, thienyl, furanyl, pyridyl, pyrimidyl, pyranyl, pyrazolyl, pyrrolyl, pyrazinyl, thiazoyl, isothiazolyl, oxazolyl, isooxazolyl, 1,2,3-trizaolyl, 1,2,4-triazolyl, and tetrazolyl.

Aryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl and isoindolyl.

An aliphatic group is a straight chained, branched or cyclic non-aromatic hydrocarbon which is completely saturated or which contains one or more units of unsaturation. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1–C4 straight chained or branched alkyl group or a C3–C8 cyclic alkyl group is also referred to as a "lower alkyl" group.

An "alkylene group" is represented by —(CH$_2$)$_n$—. n is an integer from 1–10, preferably 1–4.

Non-aromatic heterocyclic rings are non-aromatic carbocyclic rings which include one or more heteroatoms such as nitrogen, oxygen or sulfur in the ring. The ring can be five, six, seven or eight-membered. Examples include oxazolinyl, thiazolinyl, oxazolidinyl, thiazolidinyl, tetrahydrofuranyl, tetrahyrothiophenyl, morpholino, thiomorpholino, pyrrolidinyl, piperazinyl, piperidinyl, and thiazolidinyl.

Suitable substituents for an aliphatic group, non-aromatic heterocyclic group, benzylic or an aryl group ring carbon (carbocyclic and heteroaryl, e.g., substituents such as $R_7$ and $R_8$) are those which do not substantially interfere with the anti-cancer activity of the disclosed compounds. Examples of suitable substituents include —OH, halogen (—Br, —Cl, —I and —F), —OR$^a$, —O—COR$^a$, —COR$^a$, —CN, —NO$_2$, —COOH, —SO$_3$H, —NH$_2$, —NHR$^a$, —N(R$^a$R$^b$),
—COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N (R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SO$_k$R$^a$ (k is 0, 1 or 2) and —NH—C(=NH)—NH$_2$. R$^a$–R$^d$ are each independently an aliphatic, substituted aliphatic, benzyl, substituted benzyl, aryl or substituted aryl group, preferably an alkyl, benzylic or aryl group. In addition, —N(R$^a$R$^b$), taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Preferred substituents for an imidazolyl ring carbon, e.g., substituents represented by $R_7$ and $R_8$, include C1–C4 alkyl, C1–C4 hydroxylalkyl, (C1–C4 alkyl)$_3$—Si—O—(C1–C4 alkylene), pyridyl, C1–C4 alkyl substituted with pyridyl, C1–C4 alkyl substituted with —NH-pyridyl, C1–C4 hydroxyalkyl substituted with —NH-pyridyl, C1–C4 hydroxyalkyl substituted with -pyridyl, —S(O)$_2$-(phenyl), —S(O)$_2$-(tolulyl),

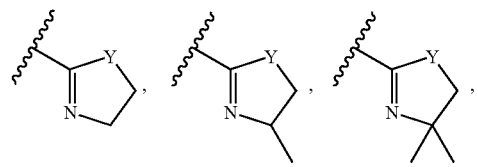

—C(O)-pyridyl, indolyl, —(C1–C4 alkylene)—O—(C1–C4 alkyl), C1–C4 alkyl substituted with —O-pyridyl, —CHO, —C(O)—O—(C1–C4 alkyl), —C(O)—NH—(C1–C4 alkyl), —C(O)—(C1–C4 alkylene)-pyridyl, oxazolinyl, —C(O)—(C1–C4 alkyl), —C=N—NH-phenyl, —C(O)—NH-pyridyl, —C(O)—NH-phenyl, —C=N—NH—(C1–C4 alkyl), —C=N—N—(C1–C4 alkyl)$_2$, —C(O)—NH—(C1–C4 alkyl), —C(O)—N—(C1–C4 alkyl)$_2$, —C(O)—(N-morphilino), —C(O)-imidazolyl, —C(O)—NH—(C1–C4 haloalkyl), —C(O)—N—(C1–C4 haloalkyl)$_2$, —CH$_2$—N$_3$, C1–C4 substituted with imidazolyl, —C1–C4 alkylene-NHC(O)—(C1–C4 alkyl), —C1–C4 alkylene-NHC(O)-(phenyl), —(C1–C4 alkylene)—NHC(O)-(tolulyl), —C1–C4-alkylene-NHC(O)-(methoxy, dimethoxy or trimethoxyphenyl). Y is —S—, —O— or —N(—H or C1–C4 alkyl or substituted alkyl)-. In the imidazolyl group represented by Structural Formula (VIII), it is especially preferred that $R_6$ and $R_7$ are both —H and $R_8$ is —C(O)NH$_2$, —C(O)CH$_3$, —C(O)CH$_2$CH$_3$, 2-pyridyl, —C(O)OCH$_3$, —C(O)OCH$_2$CH$_3$,

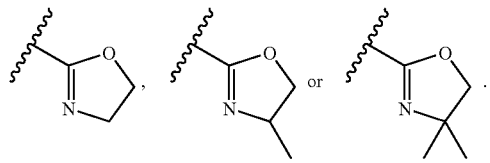

Suitable substituents for heteroaryl ring nitrogen atoms having three covalent bonds to other heteroaryl ring atoms include —OH and -alkoxy (preferably C1–C4). Substituted heteroaryl ring nitrogen atoms with three covalent bonds to other heteroaryl ring atoms are positively charged. The positive charge is balanced by counteranions. Suitable counteranions are those that are physiologically acceptable and include chloride, bromide, acetate, formate and the like. Other suitable anions are described in the section below directed to physiologically acceptable salts.

Suitable substituents for heteroaryl ring nitrogen atoms having two covalent bonds to other heteroaryl ring atoms (e.g., substituents represented by $R_6$ and $R_{10}$) an unsubstituted aliphatic group or a substituted aliphatic group, (including haloalkyl) —C(O)R$^g$, —S(O)$_2$—R$^g$ or —S(O)$_2$—N(R$^g$)$_2$. R$^g$ is a described above. Preferred substit heteroaryl ring nitrogen atoms having two covalent bonds to other heteroaryl ring atoms (e.g., substituents represented by $R_6$ and $R_{10}$) include C1–C4 alkyl, C1–C4 hydroxyalkyl, —(C1–C4 alkylene)—O—(C1–C4 alkylene)-tri(C1–C4 alkyl)silane, —S(O)$_2$N(C1–C4 alkyl)$_2$, —S(O)$_2$NH(C1–C4 alkyl) or —S(O)$_2$NH$_2$.

Preferred substituents for Rings A–F include —F, —Cl, —Br, —C1–C4 alkyl, C1–C4 alkoxy, —C1–C4 haloalkyl, C1–C4 haloalkoxy, —CN or —NH$_2$. Rings A–F can have zero, one or more substituents.

Preferred substituents for the phenyl and pyridyl ring represented by $R_3$ include —Br, —Cl, —F, —R$^e$, —OR$^e$, —CN, —COOR$^e$, —N(R$^e$)$_2$, —CON(R$^e$)$_2$, —NR$^e$COR$^f$, —NHCONH$_2$ and —SO$_2$ N(R$^e$)$_2$. Each R$^e$ and R$^f$ are independently selected from —H, alkyl or substituted alkyl. More preferred substituents for the phenyl group represented by $R_3$ include —Cl, —F, —R$^e$, —OR$^e$, —CN, —NH$_2$, —CONH$_2$ or —NHCOR$^f$. Even more preferred substituents for the phenyl group represented by $R_3$ include —CH$_3$, —CH$_2$CH$_3$, —F, —Cl, —CN or —OCH$_3$. The phenyl or pyridyl group represented by $R_3$ can have zero, one or more substituents. Preferably, the phenyl ring represented by $R_3$ is unsubstituted or monosubstituted. When substituted, the substituent is preferably at the position para to the carbon atom bonded to the methylene group.

Also included in the present invention are pharmaceutically acceptable salts of the compounds described herein. Compounds disclosed herein which possess a sufficiently acidic, a sufficiently basic, or both functional groups, and accordingly can react with any of a number of organic or inorganic bases, and inorganic and organic acids, to form a salt. Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The disclosed compounds can be used to treat subjects with cancer, including multi-drug resistant cancers. A cancer is resistant to a drug when it resumes a normal rate of tumor growth while undergoing treatment with the drug after the tumor had initially responded to the drug. A tumor "responds to a drug" when it exhibits a decrease in tumor mass or a decrease in the rate of tumor growth. The term "multi-drug resistant cancer" refers to cancer that is resistant to two or more drugs, typically five or more.

An "effective amount" is the quantity of compound in which a beneficial clinical outcome is achieved when the compound is administered to a subject with a multi-drug resistant cancer. A "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986).

Optionally, the disclosed compounds can be co-administered with other anti-cancer agents such as Taxol, Vincristine, Adriamycin, Etoposide, Doxorubicin. Dactinomycin, Mitomycin C, Bleomycin, Vinblastine, Cisplatin and the like. Preferably, the disclosed compounds are co-administered before the cancer develops multi-drug resistance or as the cancer is developing multi-drug resistance but before the cancer becomes completely resistant to the anticancer drugs being used. The method can also be carried in combination with other cancer treatments such as surgery, radiation, and the like.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The disclosed compounds can be prepared according to schemes and conditions provided in Examples 1–10.

The present invention is illustrated by the following examples, which are not intended to be limiting in any way.

EXEMPLIFICATION

Example 1

[1-(4-Trifluorobenzyl)-1H-indol-3-yl]-[1H-imidazo[4,5-c]pyridin-2-yl]methanone:

1-(2-Trimethylsilanyl-ethoxymethyl)-1H-imidazo[4,5-c]pyridine: A solution of 1H-imidazo[4,5-c]pyridine (4 g, 0.033 mol) in DMF (50 mL) was cooled in an ice bath and solid NaH (1.61 g, 0.040 mol, 60% dispersion in oil) was added in small portions. This resultant suspension was allowed to warm to room temperature and stirred for 30 minutes. The suspension was then re-cooled in an ice bath and 2-(trimethylsilyl)ethoxymethyl chloride (6.67 g, 0.040 mol) was added dropwise then stirred for overnight at room temperature. Water (100 mL) was added and the solution was extracted with ethyl acetate (3×100 mL). The ethyl acetate extracts were washed with water (5×100 mL), dried over $MgSO_4$, filtered and solvent was removed under reduced pressure to produce the crude product as a brown oil. This crude product was purified by silica gel column chromatography eluting with ethyl acetate to provide the product as a mixture of regioisomers. Light brown oil (yield 6.09 g, 74%). $R_f$ 0.4 (MeOH/ethyl acetate 1:9 v/v); $^1$H-NMR (DMSO-d6) δ -0.1 (s, 9H), 0.80–0.84 (m, 2H), 3.50–3.52 (m, 2H), 5.68&5.74 (s, 2H), 7.71 (m, 2H), 8.38 (m, 2H), 8.53&8.59 (s, 1H), 8.98&9.03 (s, 1H).

1-(4-Trifluoromethylbenzyl)-1H-indole-3-carbaldehyde: To a solution of indole-3-carbaldehyde (1 g, 6.89×10$^{-3}$ mol) and 4-trifluorobenzyl bromide (1.81 g, 7.58×10$^{-3}$ mol) in dry THF (100 mL) was added solid KOH (3 g, 0.053 mol). The resultant suspension was heated to reflux for 1 hour. After cooling to room temperature, water was added (100 mL) and the solution was extracted with ethyl acetate (3×100 mL). The combined ethyl acetate extracts were washed with water (3×50 mL) then dried over $MgSO_4$, filtered and evaporated to dryness to afford the crude product as a white solid. This crude product was purified by silcagel column chromatography eluting with ethyl acetate/hexane (1:3 v/v) to produce the pure product as a white solid (1.59 g, 76%). $R_f$ 0.5 (ethyl acetate/hexane 1:1 v/v); $^1$H NMR (CDCl$_3$) δ 5.51 (s, 2H), 7.38–7.50 (m, 4H), 7.56–7.66 (m,

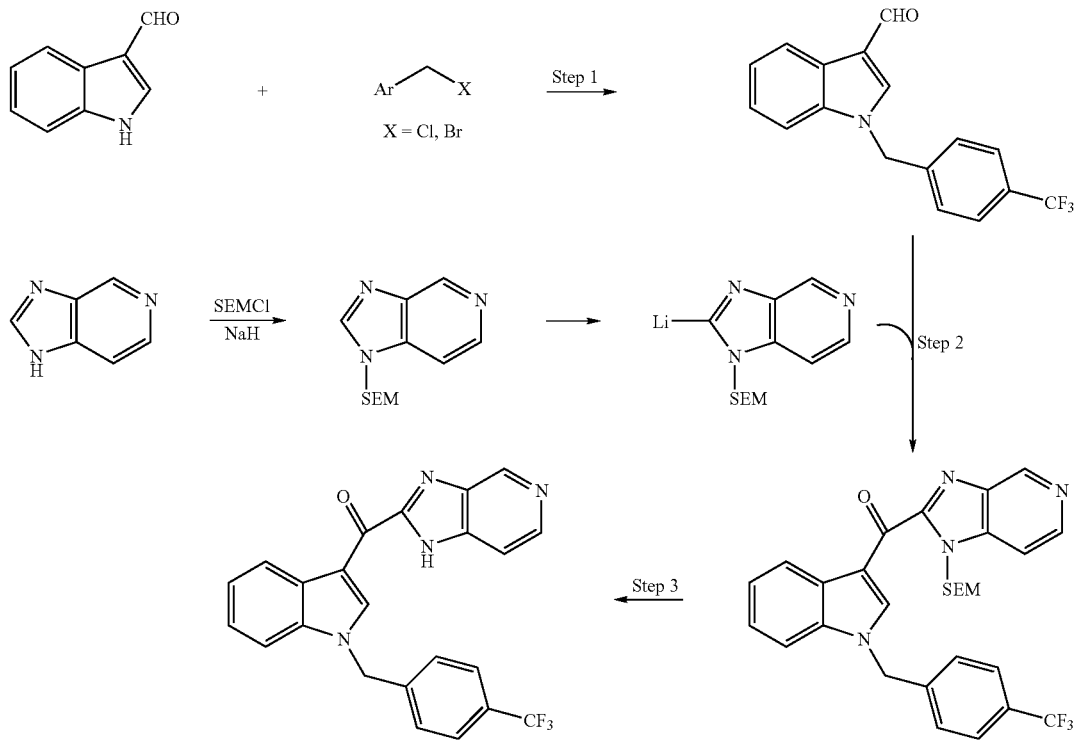

2H), 7.73 (d, J=9 Hz, 1H), 7.88 (s, 1H), 8.44–8.51 (m, 1H), 10.16 (s, 1H); ESMS Calcd ($C_{17}H_{12}F_3NO$): 303.09, found 304.1.

[1-(3,4-Dichlorobenzyl)-1H-indol-3-yl]-[1-(2-trimethyl-silanylethoxymethyl)-1H-imidazo[4,5-c]pyridin-2-yl]methanone: A solution of 1-(2-Trimethylsilanyl-ethoxymethyl)-1H-imidazo[4,5-c]pyridine (250 mg, 100×10$^{-3}$ mol) in dry THF (50 mL) was cooled to −78C in dry ice/acetone bath. To this solution was added lithium diisopropylamide (0.60 mL, 2M solution in heptane/THF/ethyl benzene, 1.20×10$^{-3}$ mol) and the reaction was stirred at −78° C. for 30 minutes. To this solution, 1-(4-trifluoromethylbenzyl)-1H-indole-3-carbaldehyde (390 mg, 1.21×10$^{-3}$ mol) dissolved in THF (20 mL) was added dropwise. The reaction was stirred at −78° C. for 1 hour, then quenched with saturated NaHCO$_3$ and allowed to warm to room temperature. The resultant solution was extracted with ethyl acetate (3×50 mL) and the ethyl acetate extracts were washed with water, dried over MgSO$_4$ and filtered. Solvent was removed under reduced pressure to produce a brown oil. This product was redissolved in CH$_2$Cl$_2$ (50 mL) and MnO$_2$ (500 mg) was added. The resultant suspension was stirred at room temperature overnight then filtered through celite. Solvent was removed under reduced pressure to produce the crude product as brown oil. Further purification by silica gel column chromatography eluting with a gradient of ethyl acetate/hexane (1:1 v/v) to ethyl acetate produced to desired product as a white solid (yield 408 mg, 74%)); $^1$H NMR (CDCl$_3$) δ 1.99 (m, 2H), 3.76 (m, 2H), 5.64 (2xs, 2H), 6.24&6.30 (2xs, 2H), 7.36–7.97 (m, 7H), 8.66–8.75 (m, 2H), 9.03&9.08 (2xs, 1H), 9.27&9.36 (2xs, 1H). ESMS Calcd ($C_{29}H_{29}F_3N_4O_2Si$): 550.20, found: 451.1 (M+H)$^+$.

[1-(3,4-Dichlorobenzyl)-1H-indol-3-yl]-[1-(2-trimethyl-silanylethoxymethyl)-1H-imidazo[4,5-c]pyridin-2-yl]methanone: A solution of [1-(3,4-Dichlorobenzyl)-1H-indol-3-yl]-[1-(2-trimethylsilanylethoxymethyl)-1H-imidazo[4,5-c]pyridin-2-yl]methanone (300 mg, 5.45×10$^{-4}$ mol) in Ethanol (50 mL) and 2N HCl (20 mL) was heated to reflux for 2 hours. After allowing to cool to room temperature, solution was neutralized with 2N NaOH and Ethanol was removed under reduced pressure. The resultant suspension was extracted with ethyl acetate (3×50 mL). The ethyl acetate extracts were washed with water (3×50 mL) and dried over MgSO$_4$ and filtered. Solvent was removed under reduced pressure to produce the pure product as a white solid. R$_f$0.3 (1:9 ethyl acetate/MeOH); $^1$H NMR (DMSO-d6) δ 5.83 (s, 2H), 7.36 (m, 2H), 7.62 (m, 4H), 7.81 (s, 1H), 8.43 (m, 2H), 9.14 (s, 1H), 9.53 (s, 1H); ESMS Calcd ($C_{23}H_{15}F_3N_4O$): 420.12, found: 421.1 (M+H)$^+$.

Example 2

[1-(4-Chloro-benzyl)-1H-indol-3-yl]-(4-pyridin-2-yl-1H-imidazol-2-yl)-methanone:

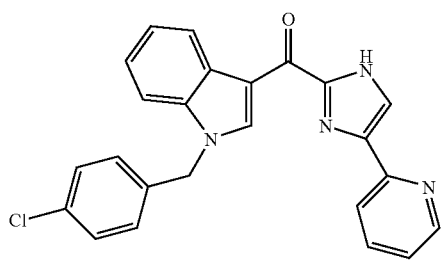

To a stirred solution of naphthalene (5.8 g, 45.3 mmol) in dry THF (20 mL) was added Na (0.85 g, 37.0 mmol) under N$_2$. After 15 minutes stirring at room temperature, the resultant green suspension was cooled to −78° C. A cooled (−78° C.) solution of 2-[5-(Toluene-4-sulfonyl)-1H-imidazol-4-yl]-pyridine (*Tetrahedron Lett.* 1976, 285) (1 g, 3.34 mmol) in dry THF (20 mL) was then added through a cannula. Stirring was continued at −78° C. for 30 minutes and then at room temperature for 10 minutes. The reaction was quenched with the addition of H$_2$O at 0° C. The reaction mixture was diluted with ethyl acetate (80 mL), washed successively with H$_2$O (50 mL) and brine (50 mL), dried over Na$_2$SO$_4$. After removal of the volatile components in vacuo, the residue was dissolved in dry DMF (5 mL) with stirring. NaH (60% with mineral oil, 0.2 g, 5.0 mmol) was then added. After stirring at room temperature for 15 minutes, a solution of SEM-Cl (0.58 g, 3.5 mmol) in dry DMF (1 mL) was then added slowly. After stirring at room temperature for 3 hours, the reaction mixture was poured into cold H$_2$O (50 mL); any undissolved materials were filtered off. The filtrate was then extracted with dichloromethane (3×30 mL) washed with H$_2$O (3×50 mL), brine (50 mL) and dried (Na$_2$SO$_4$). Flash chromatography on silica gel column (4:1 hexane/ethyl acetate to 2:1 hexane/ethyl acetate to 4:1 ethyl acetate/hexane) afforded the intermediate 2-[1-(2-trimethylsilanyl-ethoxymethyl)-1H-imidazol-4-yl]-pyridine as a colorless syrup (20.5 mg, 2.1%). $^1$H NMR (CDCl$_3$) δ 0.10 (s, 9H), 1.00 (t, 2H, J=7), 3.62 (t, 2H, J=7), 5.40(s, 2H), 7.22(t, 2H, J=4), 7.70–7.85 (m, 2H), 8.10 (d, 1H, J=6),8.65(d, 1H, J=4) ppm; the other isomer shows chemical shift at d 0.10 (s, 9H), 1.00 (t, 2H, J=7), 3.70 (t, 2H, J=7), 5.90(s, 2H), 7.22(t, 2H, J=4), 7.70–7.85 (m, 2H), 8.15 (d, 1H, J=6),8.72(d, 1H, J=4)ppm; LCMS calcd for ($C_{14}H_{21}N_3OSi$): 275.1; found: 276.1 (M+H)$^+$.

Lithium diisopropylamide (2 M solution in petane/ethyl-benzene/THF, 57 uL, 0.12 mmol) was added to a stirred solution of 2-[1-(2-trimethylsilanyl-ethoxymethyl)-1H-imidazol-4-yl]-pyridine (10.5 mg, 0.038 mmol) in dry THF (3 mL) at −78° C. under N$_2$. After 1 hour at this temperature, a solution of N-4-chlorobenzylindole-3-carboxaldehyde (31 mg, 0.12 mmol) in dry THF (1 mL) was then added through a cannula. The resultant clear solution was stirred at −78° C. for 2 hours. The temperature was then allowed to rise to room temperature and the reaction was quenched by the addition of saturated aqueous NH$_4$Cl (5 mL), extracted with dichloromethane (3×10 mL). The organic layer was separated, dried (Na$_2$SO$_4$), and concentrated under reduced pressure. Flash silica gel chromatography (4:1 hexane/ethyl acetate then 2:1 ethyl acetate/hexane then 4:1 ethyl acetate/MeOH) provided the product [1-(4-Chloro-benzyl)-1H-indol-3-yl]-[4-pyridin-2-yl-1-(2-trimethylsilanyl-ethoxymethyl)-1H-imidazol-2-yl]-methanol as a light yellow syrup (18 mg, 87%). $^1$H NMR δ −0.05 (s, 9H), 0.81 (t, 2H, J=7), 3.38 (t, 2H, J=7), 5.05–5.35 (m, 5H), 6.30 (s, 1H), 6.95–7.30 (m, 9 H), 7.45 (d, 1H, J=6), 7.65 (s, 1H), 7.71 (t, 1H, J=6), 8.05 (d, 1H, J=6), 8.60 (d, 1H, J=4)ppm; ESMS calcd for ($C_{30}H_{33}ClN_4O_2Si$): 544.2; found: 545.2 (M+H)$^+$.

A mixture of [1-(4-chloro-benzyl)-1H-indol-3-yl]-[4-pyridin-2-yl-1-(2-trimethylsilanyl-ethoxymethyl)-1H-imidazol-2-yl]-methanol (10 mg, 18.4 mmol) and (10 mg, 18.4 mmol) and MnO$_2$ (0.2 g, 2.3 mmol) in dichloromethane (5 mL) was stirred at room temperature for two hours. Flash silica gel chromatography (2:1 hexane/ethyl acetate)

afforded the oxidized product [1-(4-chloro-benzyl)-1H-indol-3-yl]-[4-pyridin-2-yl-1-(2-trimethylsilanyl-ethoxymethyl)-1H-imidazol-2-yl]-methanone as a syrup (10 mg, 100%). $^1$H NMR (CDCl$_3$) δ −0.02 (s, 9H), 0.99 (t, 2H, J=7), 3.68 (t, 2H, J=7), 5.40(s, 2H), 5.99 (s, 2H), 7.15–7.40 (m, 9H), 7.75 (t, 1H, J=4), 7.85 (d, 1H, J=6), 8.00 (s, 1H), 8.60(d, 1H, J=6), 9.00 (s, 1H)ppm; ESMS calcd for (C$_{30}$H$_{31}$ClN$_4$O$_2$Si): 542.2; found: 543.2 (M+H)$^+$.

To a stirred solution of [1-(4-Chloro-benzyl)-1H-indol-3-yl]-[4-pyridin-2-yl-1-(2-trimethylsilanyl-ethoxymethyl)-1H-imidazol-2-yl]-methanone (10 mg, 18.4 mmol) in ethanol (3 mL) was added 5 drops of concentrated HCl. The resultant solution was heated to 70° C. for 10 hours. Volatile components were then removed under reduced pressure. Pure product [1-(4-Chloro-benzyl)-1H-indol-3-yl]-(4-pyridin-2-yl-1H-imidazol-2-yl)-methanonone was precipitated out from diethyl ether (7 mg, 92%). $^1$H NMR (CD$_3$OD/THF-d$_8$): 5.7 (s, 2H), 7.2–7.5 (m, 7H), 7.9 (s, 1H), 8.45–8.65 (m, 2H), 8.85 (br, 1H), 9.85 (br, 1H). ESMS calcd for (C$_{24}$H$_{17}$ClN$_4$O): 412.1; found: 413.1 (M+H)$^+$.

Example 3

[1-(4-Chloro-benzyl)-1H-indol-3-yl]-[4-pyridin-2-yl-5-(toluene-4-sulfonyl)-1H-imidazol-2-yl]-methanone

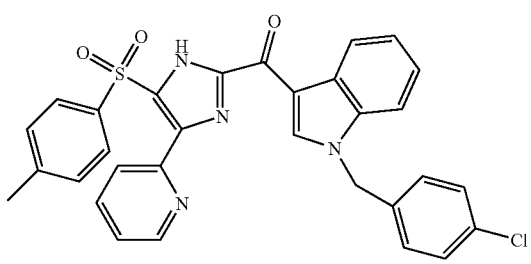

To a stirred solution of 2-[5-(toluene-4-sulfonyl)-1H-imidazol-4-yl]-pyridine (*Tetrahedron Lett.* 1976, 285) (1.65 g, 5.51 mmol) in dry DMF (15 mL) was added NaH (60% in mineral oil, 0.36 g, 9.0 mmol) at room temperature under N$_2$. After 30 minutes stirring, SEM-Cl (1.21 mL, 6.83 mmol) was added through a syringe. The slurry was further stirred at room temperature for 6 hours, and then poured into cold H$_2$O (100 mL), extracted with dichloromethane (3×50 mL). Combined dichloromethane solution was washed with H$_2$O (2×50 mL) and brine (50 mL). Flash silica gel chromatography (hexane to 2:1 hexane/ethyl acetate) afforded the 2-[5-(Toluene-4-sulfonyl)-1-(2-trimethylsilanyl-ethoxymethyl)-1H-imidazol-4-yl]-pyridin as a syrup intermediate in the forms of 1:1 regioisomers (1.89 g, 80%). $^1$H NMR δ −0.09 (s, 9H), 0.75 (t, 2H, J=7), 2.38 (s, 3H), 3.30 (t, 2H, J=7), 5.40 (s, 2H), 7.22 (d, 2H, J=8), 7.4 (t, 1H, J=6), 7.65–7.95 (m, 5 H), 8.70 (d, 1H, J=4) ppm; the other regio-isomer shows chemical shift at δ −0.02 (s, 9H), 0.8 (t, 2H, J=7), 2.41 (s, 3H), 3.41(t, 2H, J=7), 5.65 (s, 2H), 7.2–7.35 (m, 7.70–7.90 (m, 5H), 8.1 (d, 1H, J=8), 8.68 (d, 1H, J=4)ppm; (ESMS calcd for (C$_{21}$H$_{27}$N$_3$O$_3$SSI): 429.2; found: 430.4 (M+H)$^+$.

To a stirred solution of 2-[5-(toluene-4-sulfonyl)-1-(2-trimethylsilanyl-ethoxymethyl)-1H-imidazol-4-yl]-pyridine (0.15 g, 0.35 mmol) in dry THF (10 mL) was added 2.5 M n-BuLi solution in hexane (0.21 mL, 0.525 mmol) under N$_2$ at −78° C. After 20 minutes at this temperature, a solution of N-4-chlorobenzylindole-3-carboxaldehyde (0.1 g, 0.37 mmol) in dry THF (3 mL) was then added through a cannula. Stirring was continued at this temperature for 1 hour. The reaction was then quenched with H$_2$O (10 mL) at 0° C. The aqueous solution was extracted with dichloromethane (3×15 mL). Combined dichloromethane solution was washed with brine and dried over Na$_2$SO$_4$. After removal of the solvent under reduced pressure, the crude material was separated by silica gel chromatography (2:1 hexane/ethyl acetate to 2:1 ethyl acetate/hexane) to afford the desired intermediate [1-(4-chloro-benzyl)-1H-indol-3-yl]-[4-pyridin-2-yl-5-(toluene-4-sulfonyl)-1-(2-trimethylsilanyl-ethoxymethyl)-1H-imidazol-2-yl]-methanol as an oil (65 mg, 30%). $^1$H NMR (CDCl$_3$) δ −0.05 (s, 9H), 0.70 (t, 2h, J=6), 2.55 (s, 3H), 3.2–3.35 (m, 2H), 4.02 (d, 1H, J=7), 5.2–5.4 (m, 2H), 5.41 (s,2H), 6.4 (d, 1H), 7.0–8.0 (m, 16 H), 8.8 (d, 1H J=5). ESMS calcd for (C$_{37}$H$_{39}$ClN$_4$O$_4$SSi): 698.6; found: 699.6 (M+H)$^+$.

A solution of [1-(4-chloro-benzyl)-1H-indol-3-yl]-[4-pyridin-2-yl-5-(toleune-4-sulfonyl)-1-(2-trimethylsilanyl-ethoxymethyl)-1H-imidazol-2-yl]-methanol (35 mg, 50.1 mmol) in dichloromethane was treated with excess of MnO$_2$ (0.2 g, 2.3 mmol) at room temperature for 1 hour. MnO$_2$ was then filtered off and the filtrate was concentrated under reduced pressure. Product [1-(4-Chloro-benzyl)-1H-indol-3-yl]-[4-pyridin-2-yl-5-(toluene-4-sulfonyl)-1-(2-trimethyl-silanyl-ethoxymethyl)-1H-imidazol-2-yl]-methanone was obtained as an oil (34.2 mg, 98%). $^1$H NMR (CDCl$_3$) δ 0.21 (s, 9H), 0.85 (t, 2H, J=2.50 (s, 3H), 3.55 (t, 2H, J=6), 5.54 (s, 2H), 6.13 (s, 2H), 7.25–7.55 (m, 11H), 7.91 (d, 2H, J=7), 8.05 (t, 1H, J=7), 8.65 (d, 1H, J=7), 8.85 (s, 1H), 8.95 (d, 1H, J=7). ESMS calcd for (C$_{37}$H$_{37}$ClN$_4$O$_4$Ssi): 696.6; found: 697.6 (M+H)$^+$.

To a solution of [1-(4-chloro-benzyl)-1H-indol-3-yl]-[4-pyridin-2-yl-5-(toluene-4-sulfonyl)-1-(2-trimethylsilanyl-ethoxymethyl)-1H-imidazol-2-yl]-methanone (15 mg, 21.5 mmol) in ethanol (1 mL) was added 5 drops of 2N HCl. The solution was stirred at room temperature for 18 hours. A solution of 1 M HCl in ether (0.5 mL) was then added and the reaction mixture was heated to 70° C. for 2 hours. The volatile components were then removed under reduced pressure. Flash silica gel chromatography (2:1 hexane/ethyl acetate to 1:1 hexane/ethyl acetate to ethyl acetate to 4:1 ethyl acetate/methanol) afforded the product [1-(4-chloro-benzyl)-1H-indol-3-yl]-[4-pyridin-2-yl-5-(toluene-4-sulfonyl)-1H-imidazol-2-yl]-methanone as a yellow powder (12 mg, 98%). $^1$H NMR (CDCl$_3$) δ 2.3 (s, 3H), 5.3 (s, 2H), 7.0 (d, 2H, J=7), 7.1–7.3 (m, 9H), 7.8 (t, 1H, J=7), 7.9 (d, 2H, J=7), 8.4 (d, 1H, J=7), 8.6 (s, 1H), 8.7 (d, 1H, J=7), 8.85 (s, 1H). ESMS calcd for (C$_{31}$H$_{23}$ClN$_4$O$_3$S): 566.2; found: 567.2 (M+H)$^+$.

Example 4

1-[2-[1-(4-Chlorobenzyl)-1H-indole-3-carbonyl]-1H-imidazol]-4-yl]propan-1-one:

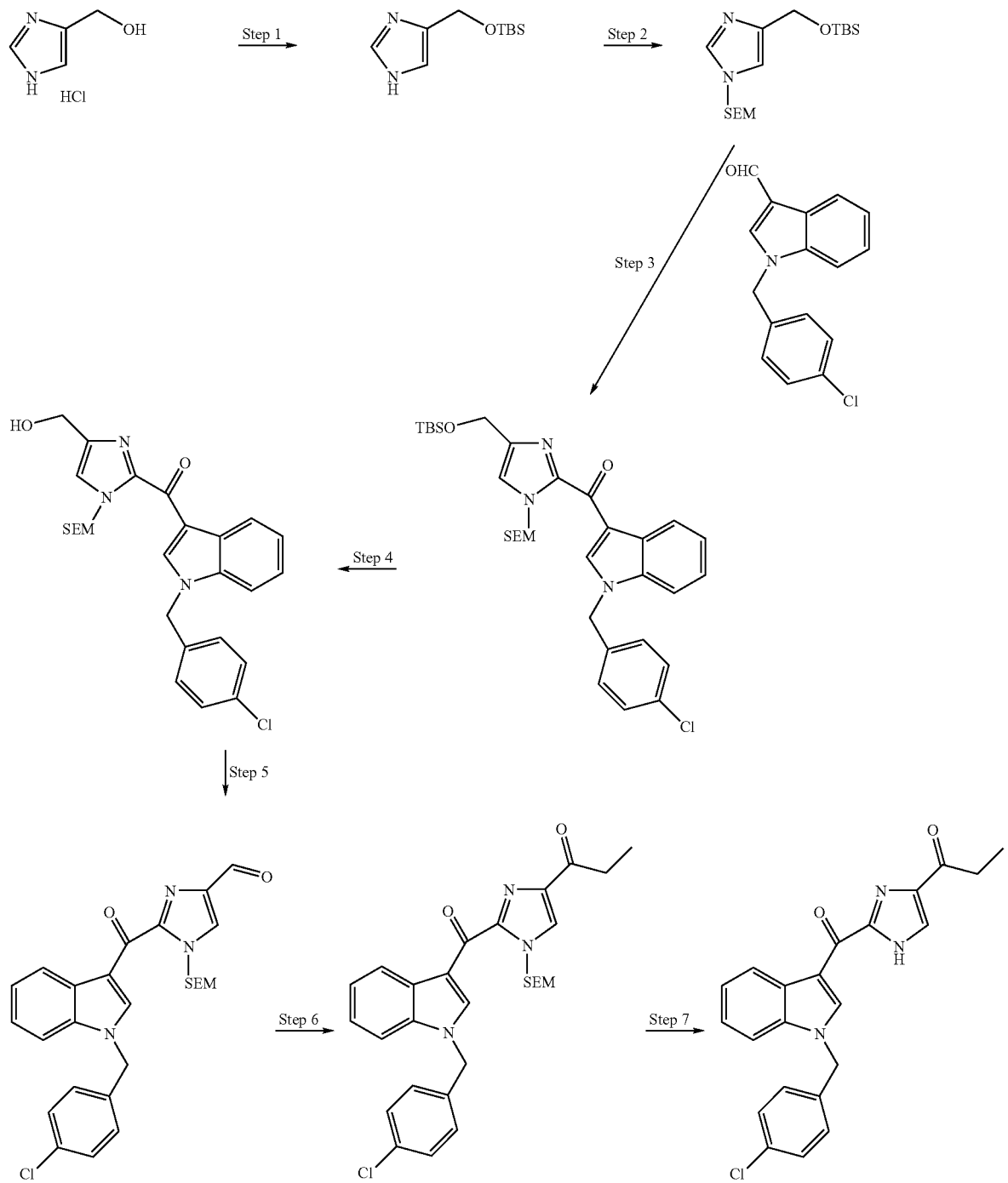

4-(t-Butyldimethylsilanyloxymethyl)-1H-imidazole: A solution of (1H-imidazol-4-yl)methanol hydrochloride (4.40 g, 0.033 mol) and imidazole (4.94 g, 0.0726 mol) in DMF (100 mL) was cooled in an ice bath. To this solution was added t-butyldimethylsilyl chloride (6.0 g, 0.040 mol) dropwise, and the reaction was stirred at room temperature overnight. The reaction mixture was poured onto saturated NaHCO$_3$ and extracted with ethyl acetate (3×100 mL). The combined ethyl acetate extracts were washed with water (5×100 mL), dried over MgSO$_4$, filtered and solvent was removed under reduced pressure to yield the crude product as a brown oil. This crude product was purified by silica gel column chromatography eluting with a gradient of ethyl acetate:hexane (1:3) to ethyl acetate. The pure product was isolated as a light brown oil which solidified upon standing (yield 10.0 g, 90%). R$_f$ 0.3 (ethyl acetate:MeOH, 9:1);

¹H-NMR (CDCl₃) d 0.04–0.08 (m, 6H), 0.86–0.90 (m, 9H), 4.72 (s, 2H), 6.94 (s, 1H), 7.61 (s, 1H), 9.67 (s, 1H); ESMS Calcd ($C_{10}H_{20}N_2OSi$): 212.13, found 213.1 (M+H)⁺.

4-(t-Butyldimethyllsilanyloxymethyl)-1-(2-trimethylsilanylethoxymethyl)-1H-imidazole: A solution of 4-(t-butyldimethyllsilanyloxymethyl)-1H-imidazole (2.48 g, 0.012 mol) in DMF (10 mL) was cooled in an ice bath. To this solution was added NaH (0.56 g, 0.014 mol, 60% dispersion in oil) in small portions. The reaction was stirred at room temperature for 30 minutes then re-cooled in an ice bath. To the resultant suspension was added (trimethylsilyl)ethoxymethyl chloride (2.20 g, 0.032 mol) dropwise and the reaction was stirred at room temperature overnight. Water (100 mL) was added and the solution was extracted with ethyl acetate (3×100 mL). The ethyl acetate extracts were washed with water (5×100 mL), dried over MgSO₄, filtered and solvent was removed under reduced pressure to produce the crude product as a brown oil. This crude product was purified by silica gel column chromatography eluting with ethyl acetate to provide the product as a mixture of regioisomers (yield 3.62 g, 88%). R$_f$0.3 (ethyl acetate); ¹H-NMR (CDCl₃) δ −0.060–0.08 (m, 15H), 0.85–0.91 (m, 11H), 3.42–3.49 (m, 2H), 4.68&4.69 (2xs, 2H), 5.21&5.33 (2xs, 2H), 6.92&6.93 (2xs, 1H), 7.49&7.51 (2xs, 1H); ESMS Calcd ($C_{16}H_{34}N_2O_2Si_2$): 342.22, found 343.2 (M+H)⁺

[4-t-Butyldimethylsilanyloxymethyl)-1-(2-trimethylsilanylethoxymethyl)-1H-imidazol-2-yl]-[1-(4-chlorobenzyl)-1H-indol-3-yl]methanone: A solution of 4-(t-butyldimethyllsilanyloxymethyl)-1-(2-trimethylsilanylethoxymethyl)-1H-imidazole (4.11 g, 0.012 mol) in dry THF (100 mL) was cooled to −78° C. in dry ice/acetone bath. To this solution was added lithium diisopropylamide (7.2 mL, 2M solution in heptane/THF/ethyl benzene, 0.014 mol) and the reaction was stirred at −78° C. for 30 minutes. To this solution, 1-(4-chlorobenzyl)-1H-indole-3-carbaldehyde (2.49 g, $9.23 \times 10^{-3}$ mol) dissolved in THF (50 mL) was added dropwise. The reaction was stirred at −78° C. for 1 hour then quenched with saturated NaHCO₃ and allowed to warm to room temperature. The resultant solution was extracted with ethyl acetate (3×50 mL) and the ethyl acetate extracts were washed with water, dried over MgSO₄ and filtered. Solvent was removed under reduced pressure to produce a brown oil. This product was redissolved in CH₂Cl₂ (50 mL) and MnO₂ (100 mg) was added. The resultant suspension was stirred at room temperature overnight then filtered through celite. Solvent was removed under reduced pressure to produce the crude product as brown oil. Further purification by silica gel column chromatography eluting with a gradient of ethyl acetate/hexane (1:1 v/v) to ethyl acetate produced to desired product as a yellow oil (yield 4.39 g, 49%)); R$_f$0.8 (ethyl acetate:hexane 1:4); ¹H NMR; ESMS Calcd ($C_{32}H_{44}ClN_3O_3Si_2$) 609.26, found 610.2 (M+H)⁺.

[1-(4-Chlorobenzyl)-1H-indol-3-yl-]-[4-hydroxymethyl-1-(2-trimethylsilanylethoxy-methyl)-1H-imidazol-2-yl]methanone: A solution of [4-t-butyldimethylsilanyloxymethyl)-1-(2-trimethylsilanylethoxymethyl)-1H-imidazol-2-yl]-[1-(4-chlorobenzyl)-1H-indol-3-yl]methanone (4.39 g, $5.98 \times 10^{-3}$ mol) in THF (100 mL) was cooled in an ice bath. Tetrabutylammonium fluoride (6.0 mL, 1 M solution in THF, $6 \times 10^{-3}$ mol) was added dropwise and the reaction was stirred for one hour. Water (100 mL) and ethyl acetate (100 mL) were added and the organic layer was washed with water, dried over MgSO₄ and filtered. Solvent was removed under reduced pressure to produce a brown oil. Further purification by silica gel column chromatography eluting with a gradient of ethyl acetate/hexane (1:3 v/v) to ethyl acetate produced to desired product as a yellow oil. (yield 2.38 g, 81%). R$_f$0.5 (ethyl acetate:hexane); ¹H NMR; ESMS Calcd ($C_{26}H_{30}ClN_3O_3Si$) 495.17, found 496.2 (M+H)⁺.

2-[1-(4-Chlorobenzyl)-1H-indole-3-carbonyl]-1-(2-trimethylsilanylethoxymethyl)-1H-imidazole-4-carbaldehyde: To a solution of [1-(4-chlorobenzyl)-1H-indol-3-yl-]-[4-hydroxymethyl-1-(2-trimethylsilanylethoxy-methyl)-1H-imidazol-2-yl]methanone (70 mg, $1.41 \times 10^{-4}$ mol) in CH₂Cl₂ (10 mL) MnO₂ (50 mg) was added. The reaction stirred overnight at room temperature and then filtered through Celite. Solvent was evaporated under reduced pressure to produce the pure product as a yellow oil. (yield 68 mg, 81%); R$_f$0.5 (ethyl acetate:hexane 1:1); ¹H NMR (CDCl₃) δ −0.13 (s, 9H), 0.76–0.96 (m, 2H), 3.50–3.63 (m, 2H), 5.29 & 5.39 (2xs, 2H), 5.86 & 6.18 (2xs, 1H), 6.98–7.06 (m, 1H), 7.14–7.35 (m, 3H), 7.56–7.66 (m, 3H), 7.76 & 7.92 (2xs, 1H), 8.49 (t, J=Hz, 1H), 8.68 & 8.94 (2xs, 1H), 9.86 & 9.91 (2xs, 1H); ESMS Calcd $C_{26}H_{28}ClN_3O_3Si$ 493.16, found 493.2 (M+H)⁺.

1-[2-[1-(4-Chlorobenzyl)-1H-indole-3-carbonyl]-1-(2-trimethylsilanyl-ethoxymethyl)-1H-imidazol-4-yl]propan-1-one: A solution of 2-[1-(4-chlorobenzyl)-1H-indole-3-carbonyl]-1-(2-trimethylsilanylethoxymethyl)-1H-imidazole-4-carbaldehyde (131 mg, $2.65 \times 10^{-4}$ mol) in THF (10 mL) was cooled in a dry ice/acetone bath to −78° C. A solution of ethyl magnesium bromide (0.32 mL, 1 M solution in THF, $3.2 \times 10^{-4}$ mol) was added dropwise and the reaction was stirred at −78° C. for 1 hour. Water (50 mL) was added and the reaction was allowed to warm to room temperature. Ethyl acetate (100 mL) was added and the organic layer was washed with water, dried over MgSO₄ and filtered. Solvent was removed under reduced pressure to produce a brown oil. Further purification by silica gel column chromatography eluting with a gradient of ethyl acetate/hexane (1:3 v/v) to ethyl acetate to ethyl acetate:methanol (1:9) produced a yellow oil. This oil was redissolved in CH₂Cl₂ (100 mL) and MnO₂ (100 mg) was added. The reaction stirred overnight at room temperature and then filtered through Celite. Solvent was evaporated under reduced pressure to produce the pure product as a yellow oil (yield 60 mg, 43%). ¹H NMR (CDCl₃) δ −0.25–0.13 (m, 9H), 0.78–0.91 (m, 5H), 1.69–1.80 (m, 2H), 3.46–3.53 (m, 2H), 5.25 (s, 2H), 5.75 (s, 2H), 7.01 (d, 2H), 7.12–7.26 (m, 6H), 8.42 (d, 1H), 8.71 (s, 1H); ESMS Calcd $C_{28}H_{32}ClN_3O_3Si$ 521.19, found 522.1 (M+H)⁺.

1-[2-[1-(4-Chlorobenzyl)-1H-indole-3-carbonyl]-1H-imidazol]-4-yl]propan-1-one: A solution of 1-[2-[1-(4-chlorobenzyl)-1H-indole-3-carbonyl]-1-(2-trimethylsilanyl-ethoxymethyl)-1H-imidazol-4-yl]propan-1-one (60 mg, $1.15 \times 10^{-4}$ mol) in ethanol (5 mL) and 2N HCl (5 mL) was heated to reflux for 2 hours. The solution was allowed to cool to room temperature then neutralized with 2N NaOH. Solvent was removed under reduced pressure and ethyl acetate (50 mL) was added. The organic layer was washed with water, dried over MgSO₄ and filtered. Solvent was removed under reduced pressure to produce a white powder (50 mg, 85%). ¹H NMR (CDCl₃) δ 1.25 (t, 3H), 3.04 (q, 2H), 5.47 (s, 2H), 7.30 (m, 6H), 7.92 (s, 1H), 8.57 (d, 1H), 9.27 (s, 1H); ESMS Calcd ($C_{22}H_{18}ClN_3O_2$): 391.1 1, found 392.1 (M+H)⁺.

Example 5

[1-(4-Chlorobenzyl)-1H-indol-3-yl]-[4-(pyridine-3-carbonyl)-1H-imidazol-2-yl]methanone

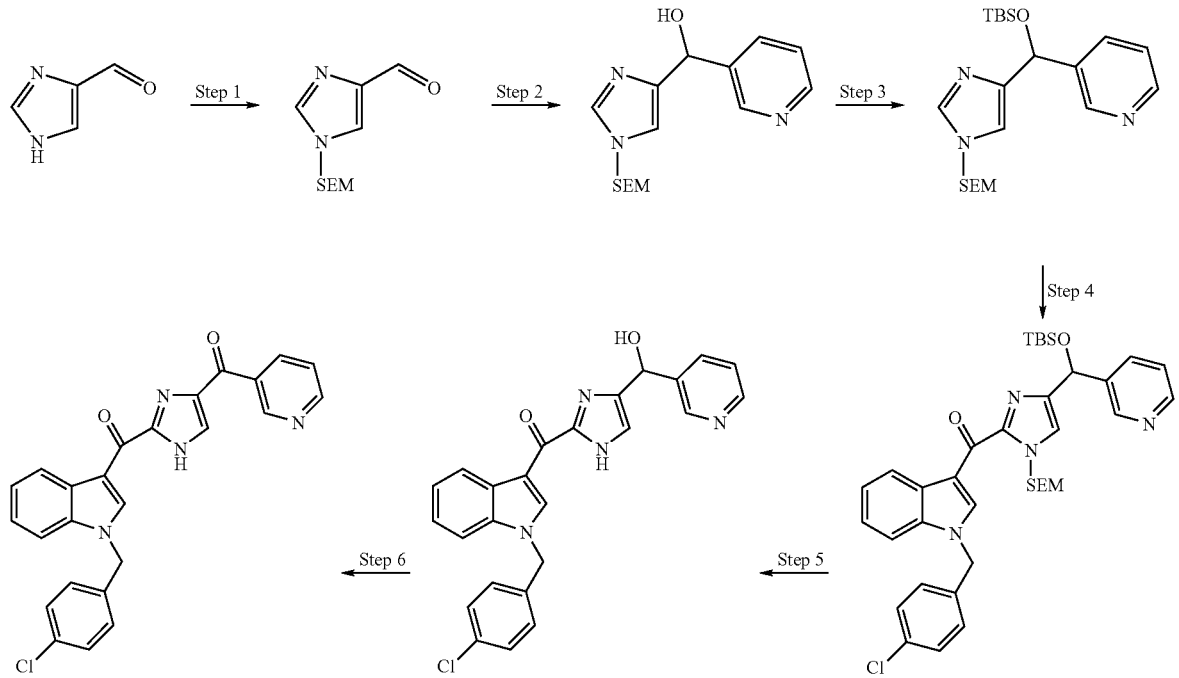

1-(2-Trimethylsilanylethoxymethyl)-1H-imidazole-4-carbaldehyde: A solution of 1H-imidazole-4-carbaldehyde (1.0 g, 0.010 mol) in DMF (20 mL) was cooled in an ice bath. To this solution was added NaH (0.48 g, 0.012 mol, 60% dispersion in oil) in small portions. The reaction was stirred at room temperature for 30 minutes and re-cooled in an ice bath. To the resultant suspension was added (trimethylsilyl) ethoxymethyl chloride (2.0 g, 0.012 mol) dropwise and the reaction was stirred at room temperature overnight. Water (50 mL) was added and the solution was extracted with ethyl acetate (3×50 mL). The ethyl acetate extracts were washed with water (5×50 mL), dried over MgSO$_4$, filtered and solvent was removed under reduced pressure to produce the crude product as a brown oil. This crude product was purified by silica gel column chromatography eluting with ethyl acetate to provide the product product as a mixture of regioisomers. R$_f$0.5 (ethyl acetate); $^1$H-NMR (CDCl$_3$) d–0.08–0.12 (m, 9H), 1.04 (t, J=8.7 Hz, 2H), 3.61–3.71 (m, 2H), 5.46&5.82 (2xs, 2H), 7.81&7.85 (2xs, 1H), 7.94&7.97 (2xs, 1H), 9,91&10.03 (2xs, 1H) ESMS Calcd (C$_{10}$H$_{18}$N$_2$O$_2$Si): 226.11, found 227.1 (M+H)$^+$.

Pyridin-3-yl-[1-(2-trimethylsilanylethoxymethyl)-1H-imidazol-4-yl]methanol: A solution of 3-bromopyridine (1.0 g, 6.33×10$^{-3}$ mol) was cooled to –78° in a dry ice/acetone bath. To this solution, BuLi (3.48 mL, 6.96×10$^{-3}$ mol, 2M solution in cyclohexane) was added dropwise and the reaction was stirred for 15 minutes. A solution of 1-(2-trimethylsilanylethoxymethyl)-1H-imidazole-4-carbaldehyde (0.955 g, 4.22×10$^{-3}$ mol) in ether (5 mL) was added dropwise to the reaction and the solution was stirred for 1 hour at –78 C. The reaction was quenched with sat. NaHCO$_3$ (10 mL) and allowed to warm to room temperature. Ethyl acetate was added (100 mL) and the organic layer was washed with water (3×50 mL), dried over MgSO$_4$, filtered and solvent was removed under reduced pressure. The crude product was purified by silcagel column chromatography eluting with a gradient of ethyl acetate:hexane (1:3) to ethyl acetate to ethyl acetate:methanol (9:1). The pure product was isolated as a mixture of isomers (yellow oil, yield 778 mg, 40%). R$_f$0.5 (ethyl acetate); $^1$H-NMR (CDCl$_3$) δ –0.09–0.11 (m, 9H), 0.86–0.99 (m, 2H), 3.41–3.57 (m, 2H), 5.22 & 5.26 (2xs, 2H), 5.89 & 6.05 (2xs, 1H), 6.63 & 6.80 (2xs, 1H), 7.25–7.39 (m, 1H), 7.53 & 7.58 (2xs, 1H), 7.79–7.90 (m, 1H), 8.53 & 8.57 (d, 1H), 8.64 & 8.69 (2xs, 1H); ESMS Calcd (C$_{10}$H$_{18}$N$_2$O$_2$Si): 226.11, found 227.1 (M+H)$^+$.

3-[(t-Butyldimethylsilanyloxy)-[1-(2-trimethylsilanylethoxymethyl)-1H-imidazol-4-yl]methyl]pyridine: A solution of pyridin-3-yl-[1-(2-trimethylsilanylethoxymethyl)-1H-imidazol-4-yl]methanol (778 mg, 2.55×10$^{-3}$ mol) and imidazole (210 mg, 3.06×10$^{-3}$ mol) in DMF (10 mL) was cooled in an ice bath. To this solution was added t-butyldimethylsilyl chloride (440 mg, 3.06×10$^{-3}$ mol) and the reaction was stirred at room temperature overnight. Saturated NaHCO$_3$ was added and the resultant solution was extracted with ethyl acetate (3×50 mL). The ethyl acetate extracts were combined and washed with water (3×50 mL), dried over MgSO$_4$, filtered and solvent was removed under reduced pressure. The crude product was purified by silcagel column chromatography eluting with a gradient of ethyl acetate:hexane (1:3) to ethyl acetate. The pure product was isolated as a mixture of isomers (yellow oil, yield 736 mg, 69%). R$_f$0.3 (ethyl acetate: methanol 9: 1); $^1$H-NMR (CDCl$_3$) d–0.02–0.16 (m, 15 H), 0.94–1.04 (m, 11H), 3.54 (t, J=8.7 Hz, 2H), 5.29 (s, 2H), 5.95& 6.11 (2xs, 1H), 7.04 & 7.11 (2xs, 1H), 7.28–7.37 (m, 1H), 7.59 & 7.65 (2xs, 1H), 7.84–7.91 (m, 1H), 8.54–8.64 (m, 1H), 8.74–8.81 (m, 1H), ESMS Calcd ($C_{15}H_{23}N_3O_2Si$): 305.15, found 306.1 $(M+H)^+$.

[4-(t-Butyldimethylsilanyloxy)pyridin-3-yl-methyl]-1-(2-trimethylsilanylethoxymethyl)-1H-imidazol-2-yl]-[1-(4-clorobenzyl)-1H-indol-3-yl]methanone: A solution of 3-[(t-butyldimethylsilanyloxy)-[1-(2-trimethylsilanylethoxymethyl)-1H-imidazol-4-yl]methyl]pyridine (530 mg, $1.26 \times 10^{-3}$ mol) in dry THF (10 mL) was cooled to –78 C in dry ice/acetone bath. To this solution was added lithium diisopropylamide (0.70 mL, 2M solution in heptane/THF/ethyl benzene, $1.39 \times 10^{-3}$ mol) and the reaction was stirred at –78° C. for 30 minutes. To this solution, 1-(4-chlorobenzyl)-1H-indole-3-carbaldehyde (0.51 g, $1.89 \times 10^{-3}$ mol) dissolved in THF (10 mL) was added dropwise. The reaction was stirred at –78° C. for 1 hour then quenched with saturated $NaHCO_3$ and allowed to warm to room temperature. The resultant solution was extracted with ethyl acetate (3×50 mL) and the ethyl acetate extracts were washed with water, dried over $MgSO_4$ and filtered. Solvent was removed under reduced pressure to produce a brown oil. This product was redissolved in $CH_2Cl_2$ (50 mL) and $MnO_2$ (100 mg) was added. The resultant suspension was stirred at room temperature overnight then filtered through celite. Solvent was removed under reduced pressure to produce the crude product as brown oil. Further purification by silica gel column chromatography eluting with a gradient of ethyl acetate/hexane (1:1 v/v) to ethyl acetate produced to desired product as a yellow oil (yield 180 mg, 21%)). $R_f$ 0.6 (ethyl acetate); $^1$H NMR ($CDCl_3$) δ –0.06–0.27 (m, 15 H), 1.96–1.09 (m, 11H), 3.75 (t, J=8.7 Hz, 2H), 5.40 & 5.47 (2xs, 2H), 5.89–6.26 (m, 3H), 7.12–7.46 (m, 9H), 7.80–7.94 (m, 1H), 8.55–8.68 (m, 2H), 8.83–8.95 (m, 2H), ESMS Calcd ($C_{15}H_{23}N_3O_2Si$): 305.15, found 306.1 $(M+H)^+$.

[1-(4-Chlorobenzyl)-1H-indol-3-yl-[4-(hydroxypyridin-3-yl-methyl)-1H-imidazol-2-yl]methanone: To a solution of [4-(t-butyldimethylsilanyloxy)pyridin-3-yl-methyl]-1-(2-trimethylsilanylethoxymethyl)-1H-imidazol-2-yl]-[1-(4-clorobenzyl)-1H-indol-3-yl]methanone (50 mg, $7.27 \times 10^{-5}$ mol) in THF (5 mL) was added tetrabutylammonium fluoride (0.22 mL, $2.81 \times 10^{-4}$ mol, 1 M solution in THF) and the solution was heated to reflux for 3 hours. Solvent was removed under reduced pressure and water (10 mL) and ethyl acetate (50 mL) was added. The organic layer was washed with water (3×10 mL), dried over $MgSO_4$ and filtered. Solvent was removed under reduced pressure to produce the crude product as a yellow oil. Further purification by silica gel column chromatography eluting with a gradient of ethyl acetate/hexane (1:1 v/v) to ethyl acetate to ethyl acetate:methanol (9:1) produced the pure product as white solid (yield 31 mg, 97%); $R_f$ 0.4 (ethyl acetate:methanol, 9:1); $^1$H NMR ($CDCl_3$) δ 5.30 (s, 2H), 5.97 (s, 1H), 7.14 (m, 2H), 7.28 (m, 4H), 7.50 (d, 1H), 7.67 (m, 1H), 8.56 (m, 2H), 9.23 (s, 1H); ESMS Calcd ($C_{25}H_{19}ClN_4O_2$): 442.12, found 443.1 $(M+H)^+$.

[1-(4-Chlorobenzyl)-1H-indol-3-yl]-[4-(pyridine-3-carbonyl)-1H-imidazol-2-yl]methanone: To a solution of [1-(4-chlorobenzyl)-1H-indol-3-yl-[4-(hydroxypyridin-3-yl-methyl)-1H-imidazol-2-yl]methanone (20 mg, $4.5 \times 10^{-5}$ mol) in $CH_2Cl_2$ (5 mL) was added $MnO_2$ (50 mg). The reaction was stirred for 1 hour at room temperature and filtered through celite to produce the desired product as a white solid (yield 15 mg, 75%). $R_f$ 0.5 (ethyl acetate:methanol, 9:1); $^1$H NMR δ 5.61 (s, 2H), 7.36 (m, 6H), 7.61 (m, 1H), 7.68 (m, 1H), 8.28 (s, 1H), 8.39 (m, 1H), 8.60 (d, 1H), 8.86 (d, 1H), 9.16 (s, 1H), 9.40 (s, 1H); ESMS Calcd ($C_{25}H_{17}ClN_4O_2$): 440.10, found 441.2 $(M+H)^+$.

Example 6

[1-(4-Chlorobenzyl)-1H-indol-3-yl]-[4-(pyridin-3-ylaminomethyl)-1H-imidazol-2-yl]methanone

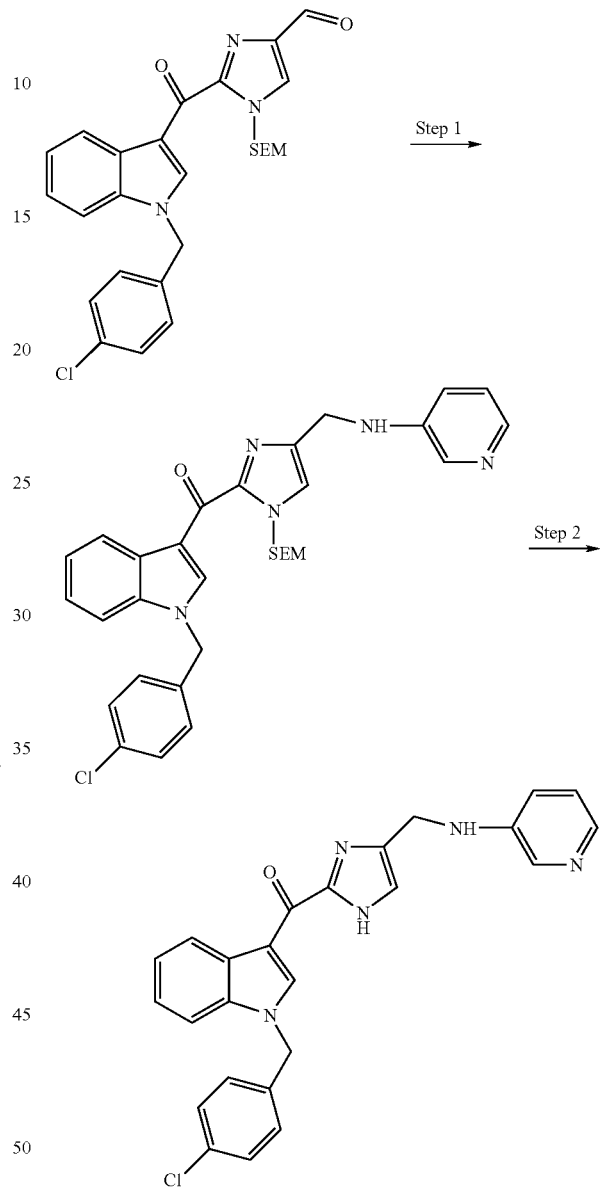

[1-(4-Chlorobenzyl)-1H-indol-3-yl]-[4-(pyridin-3-ylaminomethyl)-1-(2-trimethylsilanylethoxymethyl)-1H-imidazol-2-yl]methanone: To a solution of the starting material aldehyde (110 mg, $2.23 \times 10^{-4}$ mol) in $CH_2Cl_2$ (10 mL) was added 3-aminopyridine (31 mg, $3.34 \times 10^{-4}$ mol) and sodium triacetoxyborohydride (70 mg, $3.34 \times 10^{-4}$ mol). The reaction was stirred for 48 hours at room temperature. Saturated $NaHCO_3$ (10 mL) then ethyl acetate (50 mL) were added and the organic layer was washed with water, dried over $MgSO_4$ and filtered. Solvent was removed under reduced pressure to produce a brown oil. Further purification by silica gel column chromatography eluting with a gradient of ethyl acetate/hexane (1:3 v/v) to (1:1 v/v) produced a yellow oil (yield 43 mg, 34%). [1-(4-Chlorobenzyl)-1H-indol-3-yl]-[4-

(pyridin-3-ylaminomethyl)-1H-imidazol-2-yl]methanone: A solution of [1-(4-chlorobenzyl)-1H-indol-3-yl]-[4-(pyridin-3-ylaminomethyl)-1-(2-trimetthylsilanylethoxymethyl)-1H-imidazol-2-yl]methanone (43 mg, 7.52×10$^{-5}$ mol) in ethanol (5 mL) and 2N HCl (5 mL) was heated to reflux for 2 h. The solution was allowed to cool to room temperature then neutralized with 2N NaOH. Solvent was removed under reduced pressure and ethyl acetate (50 mL) was added. The organic layer was washed with water, dried over MgSO$_4$ and filtered. Solvent was removed under reduced pressure to produce a white powder (18 mg, 54%). $^1$H NMR; ESMS Calcd $C_{25}H_{20}ClN_5O$ 441.14, found: 442.2 (M+H)$^+$.

Example 7

[1-(4-chlorobenzyl)-1H-indol-3-yl]-[5-(4,4-dimethyl-4,5-dihydro-oxazol-2-yl)-1H-imidazol-2-yl]-methanone:

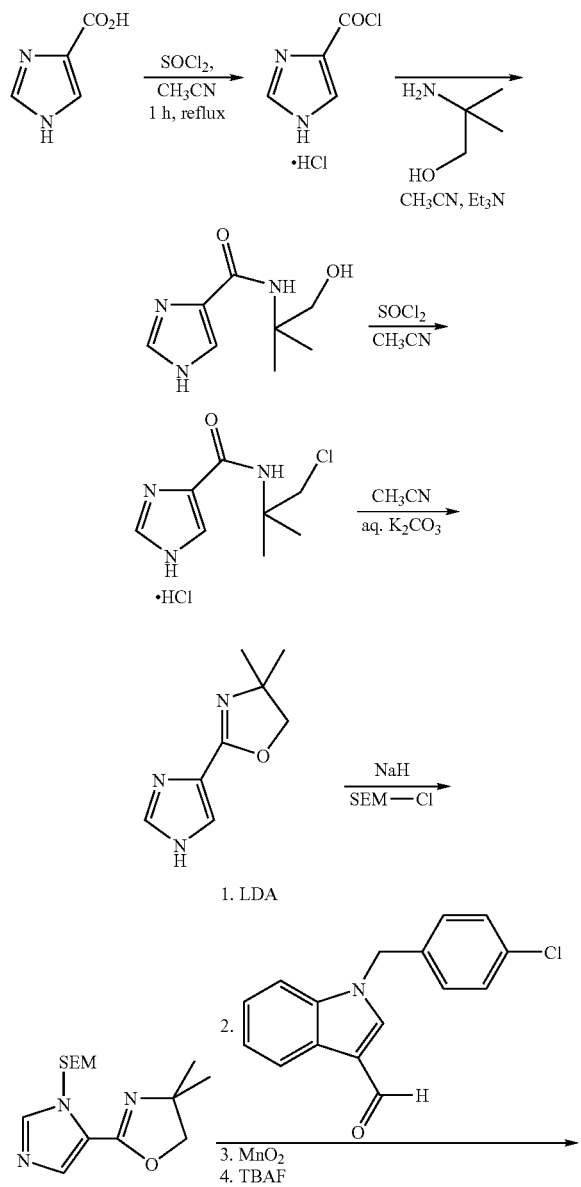

-continued

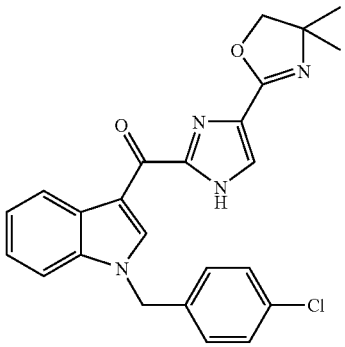

4-Imidazolecarboxylic acid (2 grams, 17.9 mmol) and thionyl chloride (5 mL, 68.5 mmol) were heated to reflux in anhydrous acetonitrile (50 mL) under nitrogen for 1 hour. Then all volatile was removed under vacuum. The conversion to acid chloride is almost quantitative. To a solution of imidazole acid chloride in anhydrous acetonitrile (10 mL) was added dropwise a solution of 2-amino-2-methyl-1-propanol (2.1 g, 21.4 mmol) and triethylamine (3.0 mL, 21.4 mmol) in anhydrous acetonitrile (10 mL) at 0° C. under N$_2$. After the addition, the ice-bath was removed and the mixture was stirred at room temperature for 5 hours. The white solid of triethylamine hydrochloride was filtered out. Solvent and excess aminoalcohol were removed under vacuum. Dark brown oil was obtained. The dark brown oil was dissolved in hot acetonitrile (20 mL). After the solution was cooled down, a solution of thionyl chloride (5 mL) in anhydrous acetonitrile (10 mL) was added dropwise at 0° C. After stirring at room temperature for 2 hours, all volatile was removed under vacuum. To the oily residue was added acetonitrile (20 mL) and 10% aqueous potassium carbonate solution (20 mL). The mixture was heated to reflux for 2 hours. Two layers were observed after the mixture was cooled down. The water layer was discarded. Sodium bicarbonate solution was added to the organic layer, and the resulting mixture was extracted with ethyl acetate 3 times. After drying over magnesium sulfate and removal of solvent, flash chromatography (ethyl acetate:methanol=4:1) yielded pure 2-(imidazol-4-yl)-4,4-dimethyloxazoline as brown oil (1.75 g, 60%). $^1$H NMR (acetone-d$_6$) δ 1.35 (s, 6H), 4.10 (s, 2H), 7.58(s, 1H), 7.85(s, 1H).

A solution of 2-(imidazol-4-yl)-4,4-dimethyloxazoline (1.74 g, 10.7 mmol) in DMF (5 mL) was added to a suspension of sodium hydride (1.2 equivalents) in DMF (5 mL) at 0° C. followed by stirring at room temperature for 1 hour. 2-(Trimethylsilyl)ethoxymethyl chloride (SEM-Cl) (2.0 g, 12 mmol) in DMF was added dropwise and the mixture was stirred overnight. Reaction mixture was poured into an aqueous solution of sodium bicarbonate followed by extraction with ethyl acetate. The combined organic extracts were washed with saturated brine, dried over magnesium sulfate and evaporated to dryness. Flash column chromatography (ethyl acetate:methanol=20:1) yielded 4,4-dimethyl-2-[1- or 3-(2-trimethylsilanyl-ethoxymethyl)-imidazol-4-yl]-oxazolines (two isomers) as brown oil (1.80 g, yield 57%). $^1$H NMR (CDCl$_3$) δ 0.10 (m, 9H), 0.92 (t, J=7.2 Hz, 2H), 1.38(s, 6H), 3.58(m, 2H), 4.02(s, 2H, isomer1), 4.60(s, 2H, isomer2), 5.38(s, 2H, isomer1), 5.82(s, 2H, isomer1), 7.62(s, 1H, isomer1), 7.75(s, 1H, isomer2), 8.01(s, 1H, isomer1), 9.22(s, 1H, isomer2).

Lithium diisopropylamide (7.2 mmol) in heptane/THF/ethyl benzene was added to a solution of 4,4-dimethyl-2-[1- or 3-(2-trimethylsilanyl-ethoxymethyl)-imidazol-4-yl]-oxazolines (1.8 g, 6.0 mmol) in THF at −78° C. The mixture was stirred at −78° C. for 30 minutes. Then a solution of pre-cooled 1-(4-chloro-benzyl)-1H-indole-3-carbaldehyde (1.5 g, 5.6 mmol) in THF was cannulated at −78° C. The mixture was stirred at room temperature for another 30 minutes followed by pouring into an aqueous solution of sodium bicarbonate and extracting with ethyl acetate. The combined organic layers were washed with brine, dried over magnesium sulfate, and evaporated to dryness. The residue was dissolved in dichloromethane and manganese dioxide (0.5 grams) was added. The resulting mixture was stirred at room temperature overnight. After filtering out all solids, the solution was evaporated to dryness. A solution of tetrabutylammonium fluoride (TBAF) (20 mmol) in THF was added, and the solution was heated to reflux overnight. The mixture was absorbed on silica gel and product [1-(4-chloro-benzyl)-1H-indol-3-yl]-[5-(4,4-dimethyl-4,5-dihydro-oxazol-2-yl)-1H-imidazol-2-yl]-methanone (970 mg, yield 40%) was collected by column chromatography (ethyl acetate:methanol=20:1). $^1$H NMR (acetone-$d_6$) δ 1.35 (m, 6H), 4.10 (s, 2H), 5.75 (s, 2 H), 7.2–7.6 (m, 7H), 7.82 (s, 1H), 8.48 (m, 1H), 9.42 (s, 1H) ppm; ESMS calcd ($C_{24}H_{21}ClN_4O_2$): 432.14; found: 433.1 (M+H)$^+$.

Example 8

2-[1-(4-chloro-benzyl)-1H-indole-3-carbonyl]-3H-imidazole-4-carboxylic acid methyl ester:

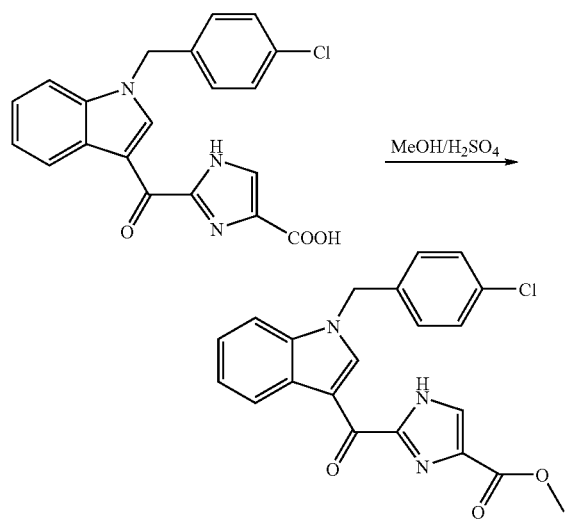

A solution of 2-[1-(4-chloro-benzyl)-1H-indole-3-carbonyl]-3H-imidazole-4-carboxylic acid (60 mg) and concentrated sulfuric acid (1 mL) in methanol (100 mL) was heated to reflux overnight. After removal of solvent, the mixture was dissolved in ethyl acetate and washed with 5% sodium hydroxide solution. The organic layers were dried over magnesium sulfate and evaporated to dryness. The product 2-[1-(4-chloro-benzyl)-1H-indole-3-carbonyl]-3H-imidazole-4-carboxylic acid methyl ester (55 mg, yield 89%) was purified by flash column chromatography (ethyl acetate: hexane=1:1). $^1$H NMR (acetone-$d_6$) δ 3.84 (s, 3H), 5.65 (s, 2H), 7.2–7.4 (m, 6 H), 7.48 (m, 1H), 7.95 (s, 1H), 8.45 (m, 1H), 9.48 (s, 1H) ppm; ESMS calcd ($C_{21}H_{16}ClN_3O_3$): 393.09; found: 394.1 (M+H)$^+$.

Example 9

{2-[1-(4-Chloro-benzyl)-1H-indole-3-carbonyl]-3H-imidazol-4-yl}-morpholin-4-yl-methanone:

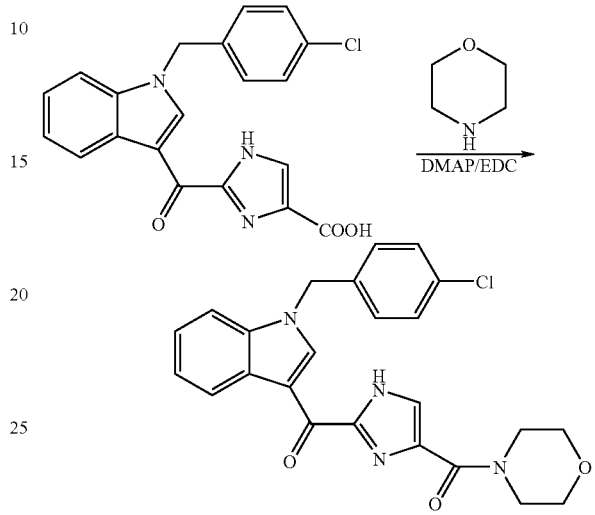

A mixture of 2-[1-(4-chloro-benzyl)-1H-indole-3-carbonyl]-3H-imidazole-4-carboxylic acid (10 mg, 0.026 mmol), 4-(dimethylamino)pyridine (DMAP) (30 mg, 0.25 mmol) and 1-(3-dimethylaminopropyl)-3-ethylcarbodiimide hydrochloride (EDC) (30 mg, 0.16 mmol) in $CH_2Cl_2$ (2 mL) was stirred at room temperature under $N_2$ for 1 hour. Then morpholine (0.1 mL) in $CH_2Cl_2$ (2 mL) was added followed by stirring overnight at room temperature. After removal of solvent, product {2-[1-(4-Chloro-benzyl)-1H-indole-3-carbonyl]-3H-imidazol-4-yl}-morpholin-4-yl-methanone (8 mg, yield 68%) was purified by column chromatography (ethyl acetate:methanol=10:1). $^1$H NMR ($CD_3OD$) δ 3.7 (m, 8H), 5.58 (s, 2H), 7.3–7.45 (m, 7 H), 7.80 (s, 1H), 8.42 (m, 1H), 9.05 (s, 1H) ppm; ESMS calcd ($C_{24}H_{21}ClN_4O_3$): 448.13; found: 449.1 (M+H)$^+$.

Example 10

[1-(4-Chloro-benzyl)-1H-indol-3-yl]-[4-(phenyl-hydrazonomethyl)-1H-imidazol-2-yl]-methanone:

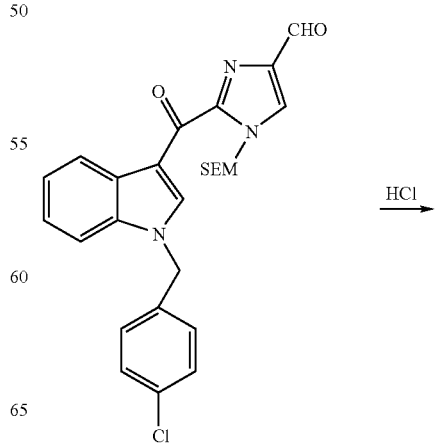

-continued

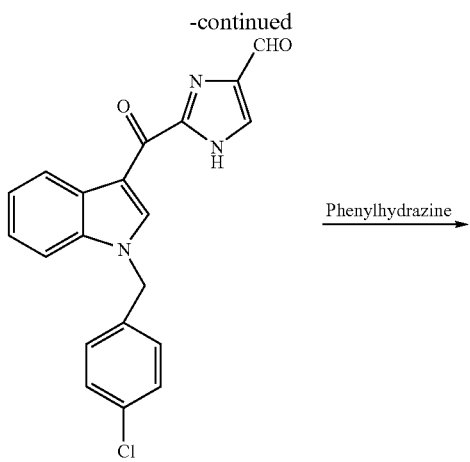

Phenylhydrazine →

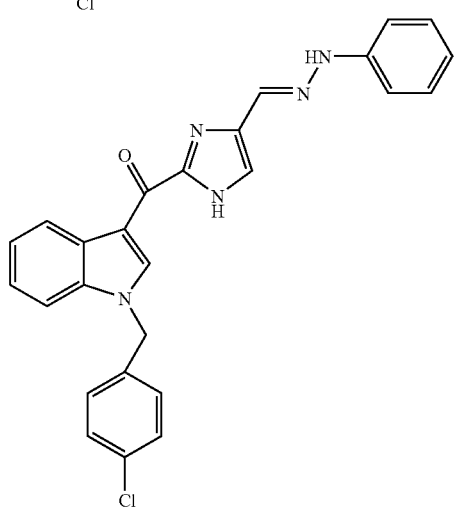

To a methanol (5 ml) solution of 2-[1-(4-chlorobenzyl)-1H-indole-3-carbonyl]-1-(2-trimetthylsilayl-methoxy)-3H-imidazole-4-carboxaldehyde (0.15 g, 0.3 mmol) was added 10% HCl (2 ml), and the mixture was refluxed for 30 minutes. After cooling the resulting solution was diluted with ethyl acetate (140 ml), and pH was adjusted to about 11 with $K_2CO_3$ and washed with water (3×20 ml). After being dried over $Na_2SO_4$, the solvent was removed under reduced pressure, and the residue was subjected to a short silica gel column chromatography (eluent: ethyl acetate in Hexanes, 30%–70%) to afford crude 2-[1-(4-chlorobenzyl)-1H-indole-3-carbonyl]-1-3H-imidazole-4-carboxaldehyde (100 mg) used for the next step. To it methanol solution (10 ml) was added 20 ml phenylhydrazine, and stirred for 10 minutes at room temperature. The solvent was removed under reduced pressure and the residue was subjected to silica gel column chromatography (eluent: ethyl acetate in Hexanes, 20%–50%) to afford [1-(4-Chloro-benzyl)-1H-ndol-3-yl]-[4-(phenyl-hydrazonomethyl)-1H-imidazol-2-yl]methanone (50 mg, total yield 37%). $^1$H NMR (CDCl$_3$) δ 5.47 (s, 2H), 6.90–7.80 (m, 13H), 8.59 (m, 2H), 9.26 (s, 1H), 10.72 (1H) ppm; ESMS calcd ($C_{20}H_{20}N_5O$): 453; found: 454 (M+H)$^+$.

Example 11

Preparation of Other Compound of the Present Invention

The compounds shown below were prepared using the methods described in Examples 1–10. Analytical data for each compound is provided.

Compound 1

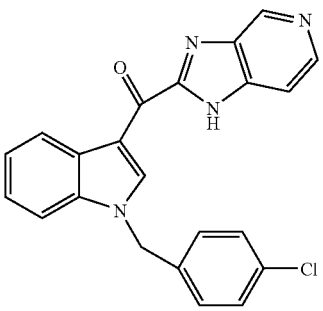

$^1$H NMR DMSO-d$_6$) δ 5.76 (s, 2H), 7.32 (m, 4H), 7.41 (d, 2H), 7.60 (d, 2H) 8.42 (d, 2H), 9.15 (s, 1H), 9.46 (s, 1H); ESMS Calcd ($C_{23}H_{16}ClN_3O$): 385.1, found 386.1 (M+H)$^+$.

Compound 2

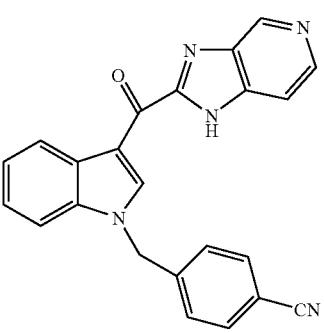

$^1$H NMR (DMSO-d$_6$) δ 5.81 (s, 2H), 7.31 (m, 2 H), 7.41 (m, 2H), 7.55 (m, 2H), 7.82 (m, 2H), 8.42 (m, 2H), 9.18 (s, 1H), 9.52 (s. 1H) ppm; ESMS calcd ($C_{20}H_{15}N_5O$): 377; found: 378(M+H)$^+$.

Compound 3

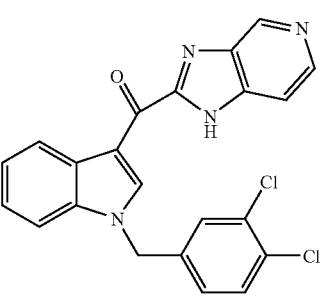

$^1$H NMR (DMSO-d$_6$) δ 5.74 (s, 2H), 7.23 (d, 2H), 7.38 (m, 2H), 7.65 (m, 3H ), 8.45 (d, 2H), 9.20 (s, 1H), 9.53 (s, 1H); ($C_{22}H_{14}C_{12}N_4O$): 420.05; found: 421.0 (M+H)$^+$.

Compound 4

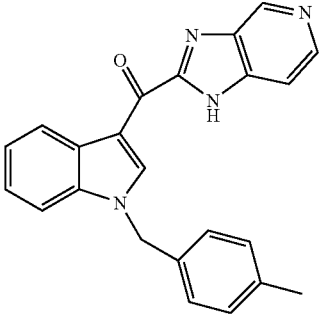

$^1$H NMR (DMSO-d$_6$) δ 2.36(s, 3H), 5.78 (s, 2H), 6.91 (m, 2 H), 7.28 (m, 4H ), 7.44 (m, 2H), 7.76 (m, 1H), 8.25 (m, 1H), 8.52 (m, 1H), 8.79 (m, 1H), 9.52 (s. 1H), 9.78 (1H) ppm; ESMS calcd (C$_{23}$H$_{18}$N$_4$O): 366; found: 367 (M+H)$^+$.

Compound 5

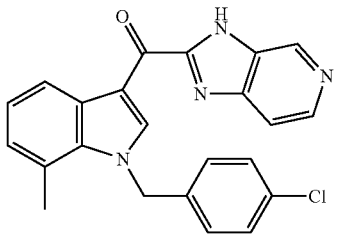

$^1$H NMR (DMSO-d$_6$) δ 2.45 (s, 3H), 5.85 (s, 2H), 7.00 (AB+m, J=7.8 Hz, 3H) 7.20 (t, J=50 Hz, 1H), 7.38 (AB, J=7.8 Hz, 2 H), 7.60 (m, 1H), 8.38 (m, 2H), 9.05 (m, 1H), 9.35(s, 1H) ppm; ESMS calcd (C$_{23}$H$_{17}$ClN$_4$O): 400.11; found: 401.0 (M+H)$^+$.

Compound 6

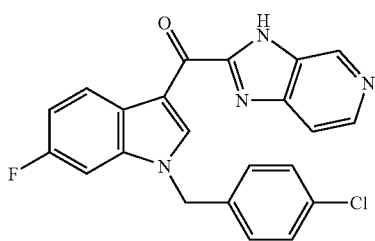

$^1$H NMR (DMSO-d$_6$) δ 5.75 (s, 2H), 7.22 (t, J=5.1 Hz, 1 H), 7.3–7.5 (AB, J=7.8 Hz, 4H), 7.60 (m, 2H), 8.41 (m, 2H), 9.18 (s, 1H), 9.45 (s, 1H) ppm; ESMS calcd (C$_{22}$H$_{14}$ClFN$_4$O): 404.08; found: 405.0 (M+H)$^+$.

Compound 7

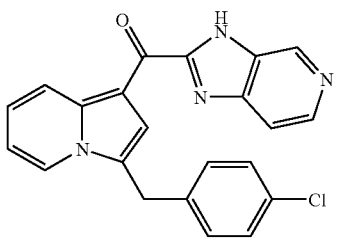

$^1$H NMR (DMSO-d$_6$) δ 4.42 (s, 2H), 7.2 (t, J=50 Hz, 1H), 7.3–7.4 (m, 3 H), 7.48 (t, J=50 Hz, 1H), 7.60 (m, 1H), 8.3–8.4 (m, 3H), 8.6 (d, J=7.8 Hz, 1H), 9.10 (s, 1H) ppm; ESMS calcd (C$_{22}$H$_{15}$ClN$_4$O): 386.09; found: 387.1 (M+H)$^+$.

Compound 8

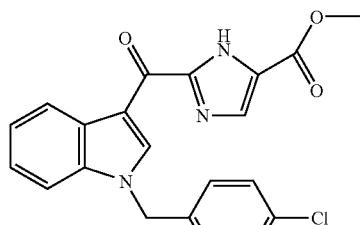

$^1$H NMR (acetone-d$_6$) δ 3.84 (s, 3H), 5.65 (s, 2H), 7.2–7.4 (m, 6 H), 7.48 (m, 1H), 7.95 (s, 1H), 8.45 (m, 1H), 9.48(s, 1H) ppm; ESMS calcd (C$_{21}$H$_{16}$ClN$_3$O$_3$): 393.09; found: 394.1 (M+H)$^+$.

Compound 9

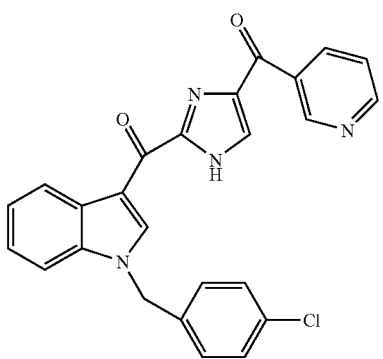

$^1$H NMR (CD$_3$OD/THF-d$_8$): δ 5.7 (s, 2H), 7.2–7.5 (m, 7H), 7.9 (s, 1H), 8.45–8.65 (m, 3H), 8.85 (br, 1H), 9.85 (br, 1H). ESMS calcd for (C$_{24}$H$_{17}$ClN$_4$O): 412.1; found: 413.1 (M+H)$^+$.

Compound 10

$^1$H NMR (DMSO-d$_6$) δ 5.61 (s, 2H), 7.36 (m, 6H), 7.61 (m, 1H), 7.68 (m, 1H ), 8.28 (s, 1H), 8.39 (m, 1H), 8.60 (d, 1H), 8.86 (d, 1H), 9.16 (s, 1H), 9.40 (s, 1H); ESMS Calcd (C$_{25}$H$_{17}$ClN$_4$O$_2$): 440.10, found 441.2 (M+H)$^+$.

Compound 11

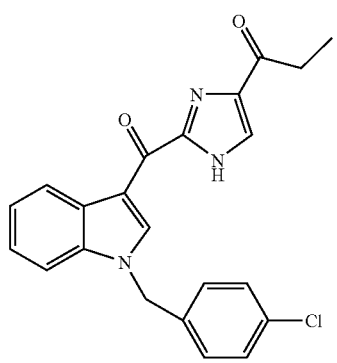

¹H NMR (CDCl₃) δ 1.25 (t, 3H), 3.04 (q, 2H), 5.47 (s, 2H), 7.30 (m, 6H), 7.92 (s, 1H), 8.57 (d, 1H), 9.27 (s, 1H); ESMS Calcd (C₂₂H₁₈ClN₃O₂): 391.11, found 392.1 (M+H)⁺.

Compound 14

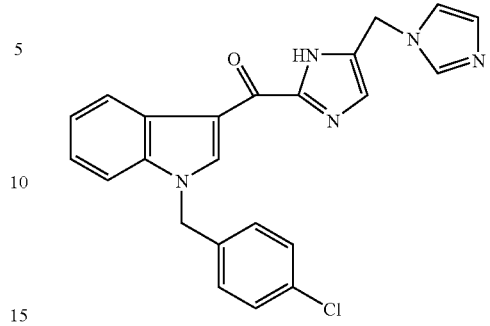

¹H NMR (CDCl₃) δ 5.16 (s, 2H), 5.42 (s, 2H), 7.20 (m, 3H), 7.34 (m, 5H), 7.64 (s, 1H), 7.71 (s, 1H), 8.50 (m, 2H), 9.22 (s, 1H). ESMS calcd (C₂₃H₁₈ClN₅O): 415.1; found: 416.1; (M+H)⁺.

Compound 12

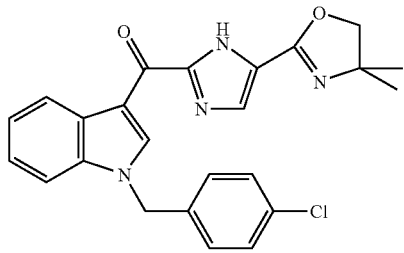

¹H NMR (acetone-d₆) δ 1.35 (m, 6H), 4.10 (s, 2H), 5.75 (s, 2H), 7.2–7.6 (m, 7H), 7.82 (s, 1H), 8.48 (m, 1H), 9.42 (s, 1H) ppm; ESMS calcd (C₂₄H₂₁ClN₄O₂): 432.14; found: 433.1 (M+H)⁺.

Compound 15

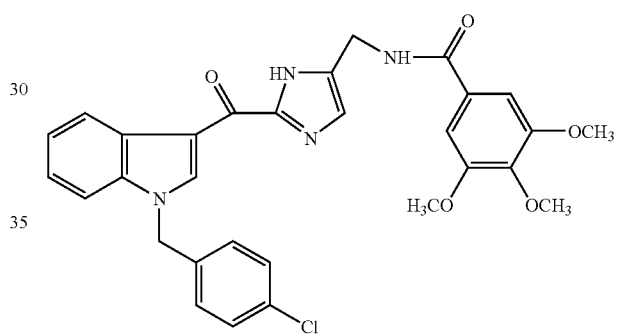

¹H NMR (CDCl₃) δ 3.96 (m, 9H), 4.64 (s, 2H), 5.42 (s, 2H), 7.22 (m, 10 H), 8.54 (d, J=7.8 Hz, 1H), 9.12 (s, 1H). ESMS calcd (C₃₀H₂₇ClN₄O₅): 558.2; found: 557.2 (M–H)⁺.

Compound 13

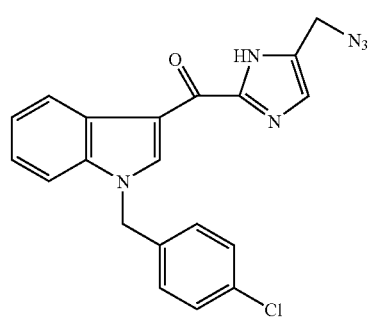

¹H NMR (CDCl₃) δ 4.30 (s, 2H), 5.42 (s, 2H), 7.22 (m, 8H), 8.52 (m, 1H), 9.28 (d, J=7.8 Hz, 1H), 11.22 (s, 1H). ESMS calcd (C₂₀H₁₅ClN₆O): 390.1; found: 391.1 (M+H)⁺.

Compound 16

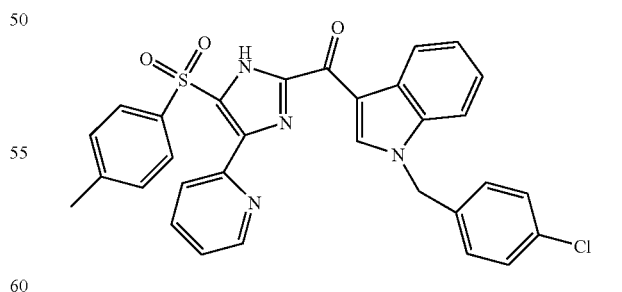

¹H NMR (CDCl₃) δ 2.3 (s, 3H), 5.3 (s, 2H), 7.0 (d, 2H, J=7), 7.1–7.3 (m, 9H), 7.8 (t, 1H, J=7), 7.9 (d, 2H, J=7), 8.4 (d, 1H, J=7), 8.6 (s, 1H), 8.7 (d, 1H, J=7), 8.85 (s, 1H). ESMS calcd for (C₃₁H₂₃ClN₄O₃S): 566.2; found: 567.2 (M+H)⁺.

Compound 17

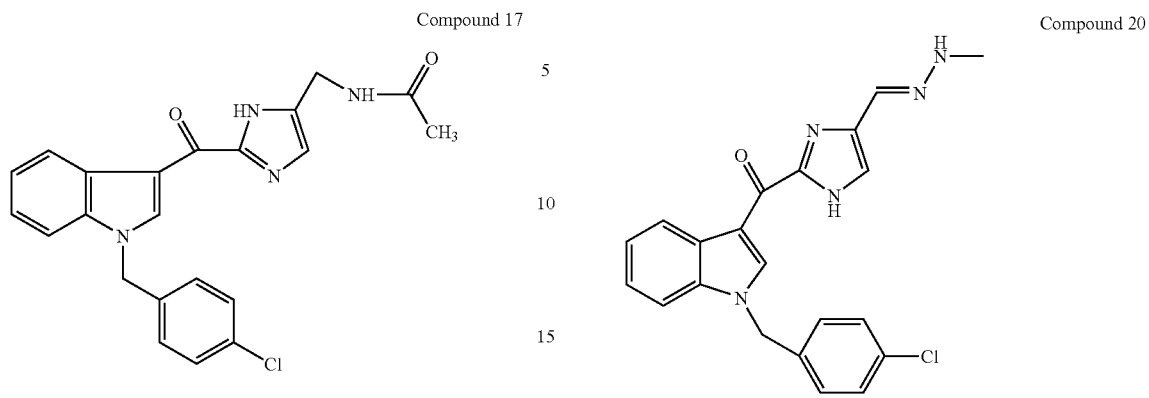

¹H NMR (CDCl₃) δ 2.24 (s, 3H), 4.40 (s, 2H), 5.42 (s, 2H), 7.24 (m, 9H), 8.53 (d, J=7.2 Hz, 1H), 9.18 (s, 1H). ESMS calcd (C₂₂H₁₉ClN₄O₂): 406.1; found: 407.1 (M+H)⁺.

Compound 18

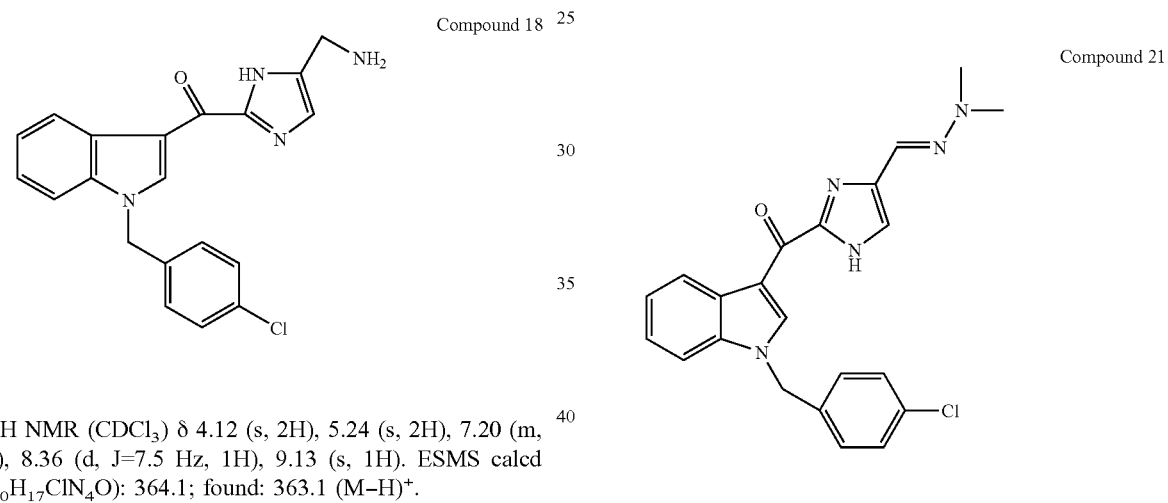

¹H NMR (CDCl₃) δ 4.12 (s, 2H), 5.24 (s, 2H), 7.20 (m, 9H), 8.36 (d, J=7.5 Hz, 1H), 9.13 (s, 1H). ESMS calcd (C₂₀H₁₇ClN₄O): 364.1; found: 363.1 (M−H)⁺.

Compound 19

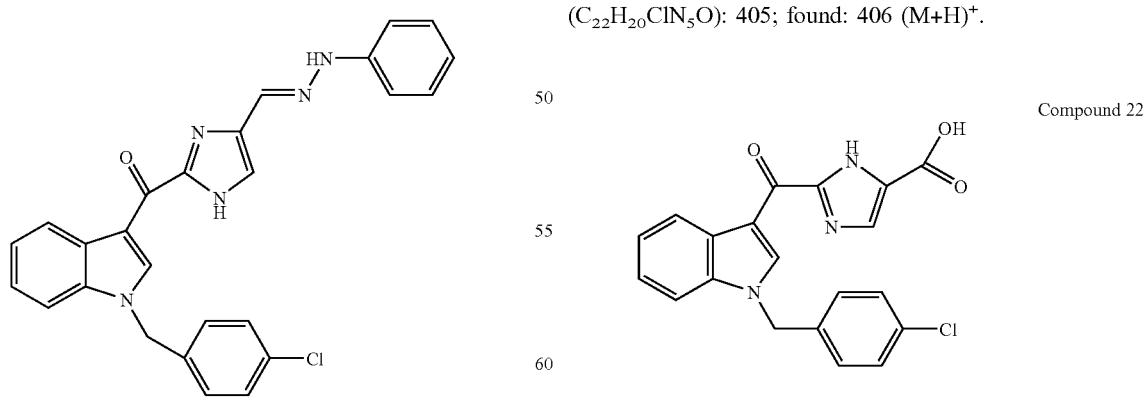

¹H NMR (CDCl₃) δ 5.47 (s, 2H), 6.90–7.80 (m, 13H), 8.59 (m, 2H), 9.26 (s, 1H), 10.72 (1H) ppm; ESMS calcd (C₂₀H₂₀N₅O): 453; found: 454 (M+H)⁺.

Compound 20

¹H NMR (CD₃OD) δ 2.95 (s, 3H), 5.41 (s, 2 H), 7.11–7.42 (m, 7H), 8.58 (m, 2H), 9.22 (m, 2H), 10.78 (1H) ppm; ESMS calcd (C₂₁H₁₈ClN₅O): 391; found: 392 (M+H)⁺.

Compound 21

¹H NMR (CD₃OD) δ 2.95 (s, 6H), 5.39 (s, 2 H), 7.05–7.78 (m, 9H), 8.59 (m, H), 9.20 (1H) ppm; ESMS calcd (C₂₂H₂₀ClN₅O): 405; found: 406 (M+H)⁺.

Compound 22

¹H NMR (DMSO-d₆) δ 5.62 (s, 2H), 7.25(AB+m, J=7.8 Hz, 3H), 7.40 (AB, J=7.8 Hz, 2H), 7.55 (m, 2 H), 7.95 (s, 1H), 8.38(m, 1H), 9.35 (s, 1H) ppm; ESMS calcd (C₂₀H₁₄ClN₃O₃): 379.07; found: 378.1 (M−H)⁺.

Compound 23

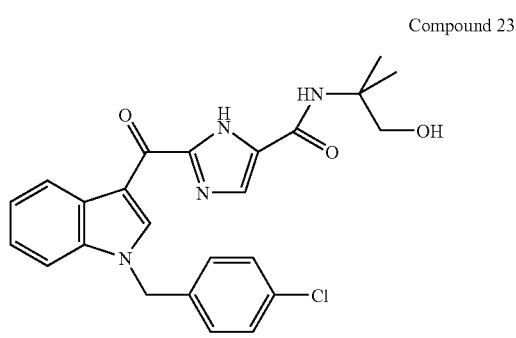

¹H NMR (CD₃OD) δ 1.45 (s, 6H), 4.38 (s, 2H), 5.55 (s, 2H), 7.2–7.4 (m, 6 H), 7.45 (m, 1H), 8.18 (s, 1H), 8.40 (m, 1H), 9.10 (s, 1H) ppm; ESMS calcd ($C_{24}H_{23}ClN_4O_3$): 450.15; found: 449.2 (M–H)⁺.

Compound 24

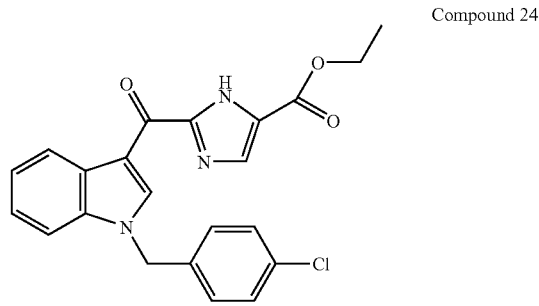

¹H NMR (CD₃OD) δ 1.40 (t, J=7.2 Hz, 3H), 4.40 (q, J=7.2 Hz, 2H), 5.55 (s, 2 H), 7.2–7.5 (m, 7H), 7.95 (s, 1H), 8.42 (m, 1H), 9.40 (s, 1H) ppm; ESMS calcd ($C_{22}H_{18}ClN_3O_3$): 407.10; found: 408.1 (M+H)⁺.

Compound 25

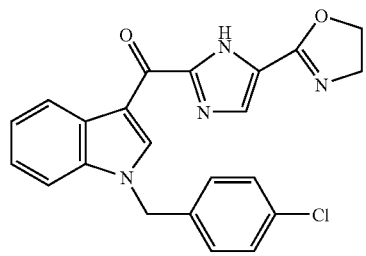

¹H NMR (CDCl₃) δ 4.10 (t, J=7.2 Hz, 2H), 4.45 (t, J=7.2 Hz, 2H), 5.45 (s, 2H), 7.0–7.4 (m, 7H), 7.80 (s, 1H), 8.55 (d, J=5.0 Hz, 1H), 9.42 (s, 1H) ppm; ESMS calcd ($C_{22}H_{17}ClN_4O_2$): 404.10; found: 405.1 (M+H)⁺.

Compound 26

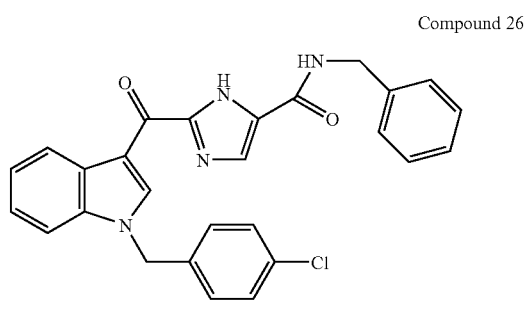

¹H NMR (acetone-d₆) δ 4.58 (d, J=4.0 Hz, 2H), 5.58 (s, 2H), 7.2–7.45 (m, 12 H), 7.95 (s, 1H), 8.25 (m, 1H), 8.45 (d, J=5.0 Hz, 1H), 9.62 (s, 1H) ppm; ESMS calcd ($C_{27}H_{21}ClN_4O_2$): 468.14; found: 469.1 (M+H)⁺.

Compound 27

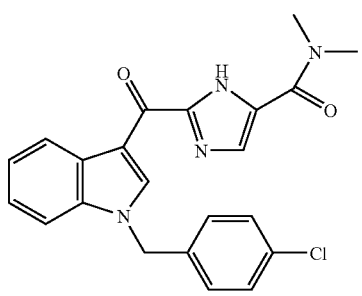

¹H NMR (acetone-d₆) δ 3.05 (s, 3H), 3.45 (s, 3H), 5.62 (s, 2 H), 7.2–7.6 (m, 7H), 7.84 (s, 1H), 8.52 (m, 1H), 9.05 (s, 1H) ppm; ESMS calcd ($C_{22}H_{19}ClN_4O_2$): 406.12; found: 407.1 (M+H)⁺.

Compound 28

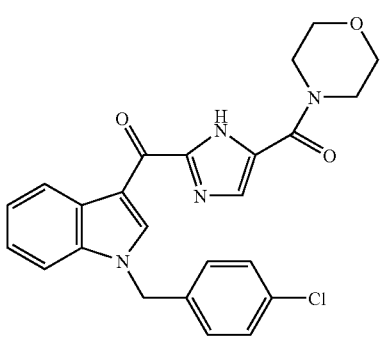

¹H NMR (CD₃OD) δ 3.7 (m, 8H), 5.58 (s, 2H), 7.3–7.45 (m, 7 H), 7.80 (s, 1H), 8.42 (m, 1H), 9.05 (s, 1H) ppm; ESMS calcd ($C_{24}H_{21}ClN_4O_3$): 448.13; found: 449.1 (M+H)⁺.

Compound 29

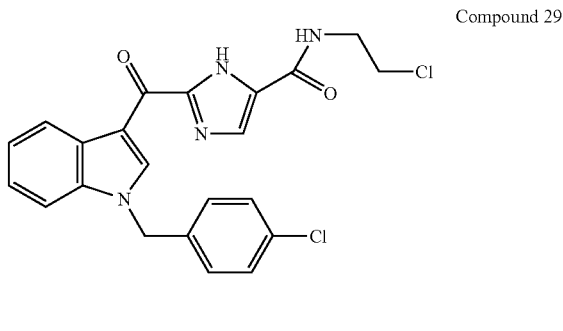

¹H NMR (CD₃OD) δ 3.87 (m, 2H), 4.38 (m, 2H), 5.55 (s, 2H), 7.2–7.4 (m, 6 H), 7.45 (m, 1H), 8.18 (s, 1H), 8.40 (m, 1H), 9.10 (s, 1H) ppm; ESMS calcd (C₂₂H₁₈Cl₂N₄O₃): 440.08; found: 439.1 (M–H)⁺.

Compound 30

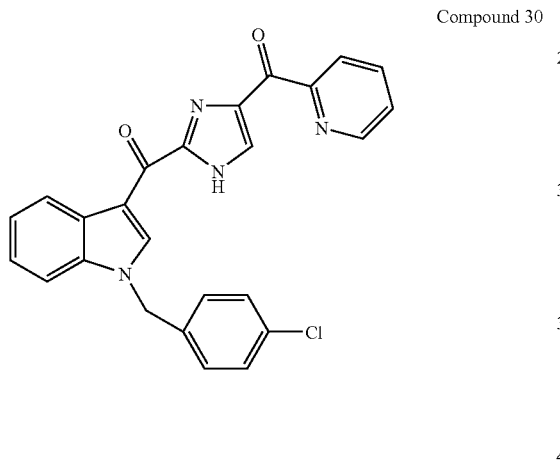

¹H NMR (DMSO-d₆) δ 5.48 (s, 2H), 7.12 (d, 2H), 7.30 (m, 5H), 7.55 (dd, 1H), 7.91 (dd, 1H), 8.31 (d, 1H), 8.60 (d, 1H), 8.86 (d, 1H), 9.34 (s, 1H); ESMS Calcd (C₂₅H₁₇ClN₄O₂): 440.10, found 441.2 (M+H)⁺.

Compound 31

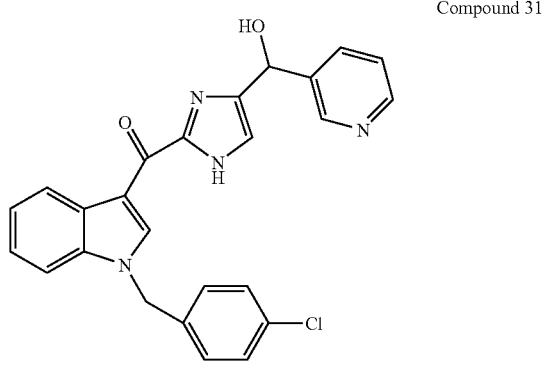

¹H NMR (DMSO-d₆) δ 5.30 (s, 2H), 5.97 (s, 1H), 7.14 (m, 2H), 7.28 (m, 4H ), 7.50 (d, 1H), 7.67 (m, 1H), 8.56 (m, 2H), 9.23 (s, 1H); ESMS Calcd (C₂₅H₁₉ClN₄O₂): 442.12, found 443.1 (M+H)⁺.

Compound 32

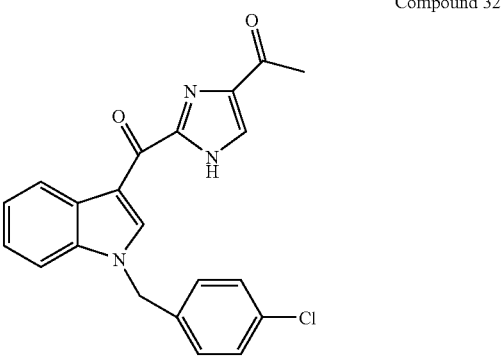

¹H NMR (CDCl₃) δ 2.58 (s, 3H), 5.47 (s, 2H), 7.30 (m, 6H), 7.85 (s, 1H), 7.56 (d, 1H), 9.25 (s, 1H); ESMS Calcd (C₂₁H₁₆ClN₃O₂): 377.09, found 378.1 (M+H)⁺.

Compound 33

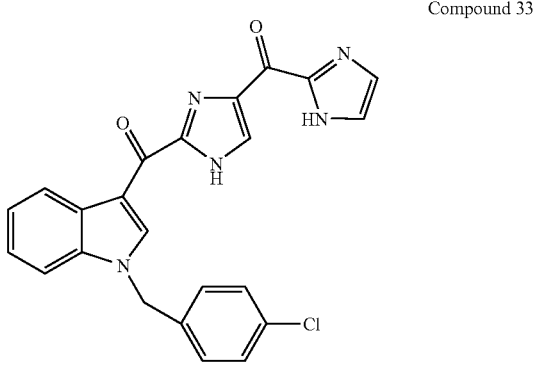

¹H NMR (DMSO-d₆) δ 5.72 (s, 2H), 7.36 (m, 6H), 7.60 (m, 1H), 8.42 (m, 1H ), 9.35 (s, 1H); ESMS Calcd (C₂₃H₁₆ClN₅O₂): 429.10, found 430.1 (M+H)⁺.

Compound 34

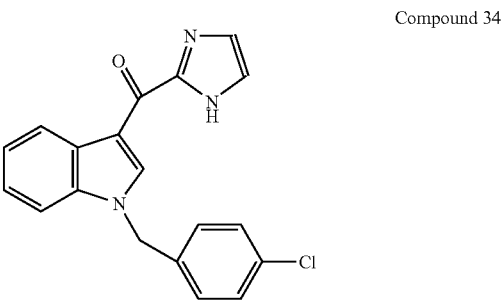

¹H NMR (DMSO-d₆) δ 5.60 (s, 2H), 7,17 (s, 1H), 7.26 (m, 3H), 7.41 (d, 2H ), 7.57 (dd, 1H), 7.65 (s, 1H), 8.18 (s, 1H), 8.20 (dd, 1H), 8.74 (s, 1H); ESMS Calcd (C₁₉H₁₄ClN₃O): 335.08, found: 336.1 (M+H)⁺.

Compound 35

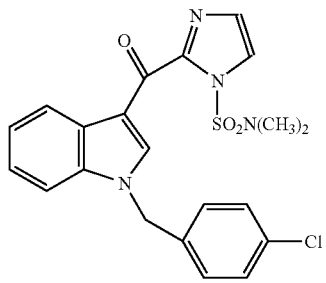

¹H NMR (DMSO-d₆) δ 3.05 (s, 6H), 5.60 (s, 2H), 7.35 (m, 7H), 7.60 (dd, 1H), 8.04 (s, 1H), 8.16 (dd, 1H), 8.51 (s, 1H); ESMS Calcd (C$_{21}$H$_{19}$ClN$_4$O$_3$S): 442.09, found: 443.1 (M+H)⁺. 305 (s, 6H), 5.60 (s, 2H), 7.35 (m, 7H), 7.60 (dd, 1H), 8.04 (s, 1H), 8.16 (dd, 1H), 8.51 (s, 1H); ESMS Calcd (C$_{21}$H$_{19}$ClN$_4$O$_3$S)\: 442.09, found: 443.1 (M+H)⁺.

Compound 36

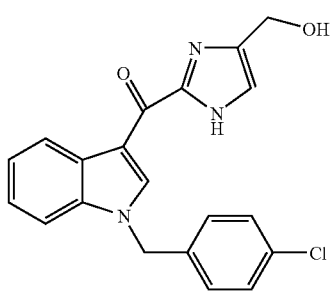

¹H NMR (DMSO-d₆) δ 4.52 (s, 2H), 5.67 (s, 2H), 7.24 (m, 5H), 7.46 (d, 2H ), 7.57 (m, 1H), 8.40 (m, 1H), 9.33 (s, 1H); ESMS Calcd (C$_{20}$H$_{16}$ClN$_3$O$_2$): 365.09, found 366.3 (M+H)⁺

Compound 37

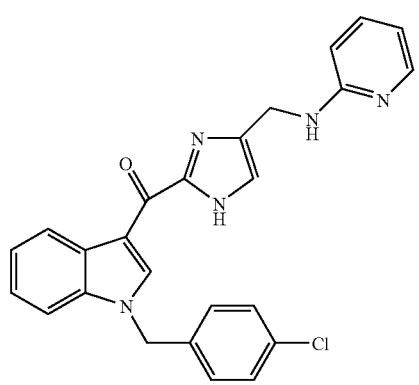

¹H NMR (DMSO-d₆) δ 4.58 (d, 2H), 5.61 (s, 2H), 6.82 (t, 1H), 7.26 (m, 5H ), 7.41 (d, 2H), 7.56 (m, 1H), 7.87 (m, 1H), 7.98 (d, 1H), 8.39 (m, 1H), 9.30 (s, 1H); ESMS Calcd (C$_{25}$H$_{20}$ClN$_5$O$_2$): 441.14, found 442.4 (M+H)⁺

Compound 38

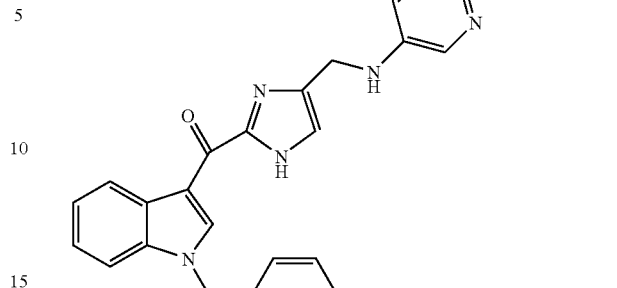

¹H NMR (DMSO-d₆) δ 4.26 (d, 2H), 5.64 (s, 2H), 6.22 (t, 1H), 7.04 (m, 2H ), 7.26 (m, 5H), 7.39 (m, 2H), 7.63 (m, 1H), 7.71 (m, 1H), 8.11 (s, 1H), 8.38 (m, 1H), 9.30 (s, 1H); ESMS Calcd (C$_{25}$H$_{20}$ClN$_5$O$_2$): 441.14, found 442.2 (M+H)⁺

Compound 39

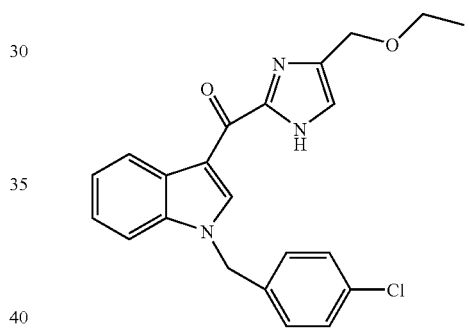

¹H NMR (CDCl₃) δ 1.30 (t, J=7.6 Hz, 3H), 3.74 (q, J=7.6 Hz, 2H), 5.37 (s, 2H), 7.30 (m, 6H), 7.82 (s, 1H), 8.57 (d, 1H), 9.27 (s, 1H); ESMS Calcd (C$_{22}$H$_{20}$ClN$_3$O$_2$): 393.11; found 394.1 (M+H)⁺.

Compound 40

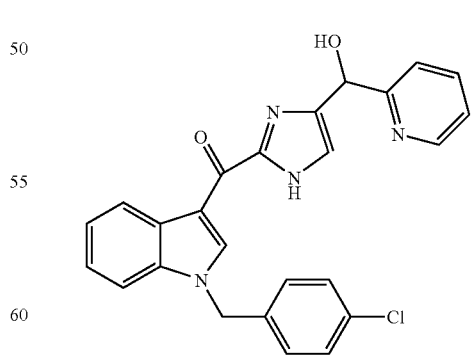

¹H NMR (CDCl₃) δ 5.35 (s, 1H), 5.93 (s, 1H), 7.09 (m, 2H), 7.46 (d, 1H), 7.50 (m, 6H), 7.64 (m, 1H), 8.51 (m, 2H), 9.18 (s, 1H); ESMS Calcd (C$_{25}$H$_{19}$ClN$_4$O$_2$): 442.12, found 443.1 (M+H)⁺.

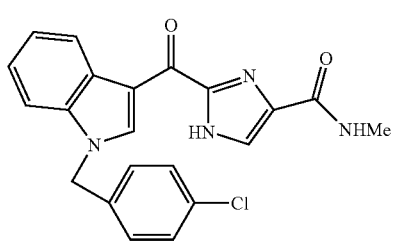

Compound 41

ESMS Calcd (C$_{21}$H$_{17}$ClN$_4$O$_2$): 392.11, found 393.1 (M+H)$^+$.

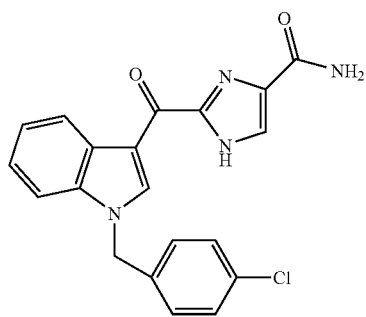

Compound 42

$^1$H NMR (CD$_3$OD) δ 9.59(s, 1H), 8.42(dd, 1H, J=6.3&1.8 Hz), 7.90 (s, 1H ), 7.35–7.15 (m, 9H), 5.69 (s, 2H); ESMS calcd (C$_{20}$H$_{15}$ClN$_4$O$_2$): 378.09; found: 379.1 (M+H)$^+$.

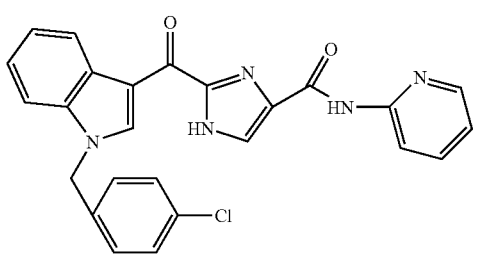

Compound 43

$^1$H NMR (DMSO-d$_6$) δ 9.98(bs,1H), 9.609(s,1H), 8.439-8.37(m,2H), 8.23(d,1H,8.4), 8.11(s,1H), 7.88(t,1H,J=8), 7.60 (m, 1H), 7.45–7.18(m,8H), 5.69(s,2H ); ESMS calcd (C$_{25}$H$_{18}$ClN$_5$O$_2$): 455.11; found: 456.1 (M+H)$^+$.

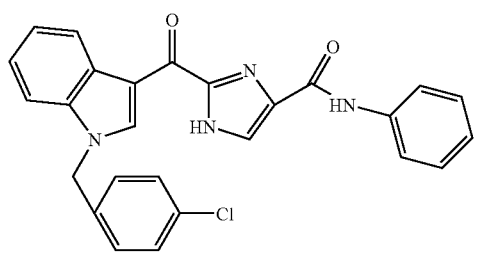

Compound 44

$^1$H NMR (DMSO-d$_6$) δ 10.01 (s,1H), 9.89(s,1H), 8.52(d, 1H,J=8.1), 8.30(d,1H,J=7.5), 8.12(s, 1H), 7.95(d,2H,J=7.5), 7.72–7.23(m,9H), 7.03(d,1H,5.7), 5.81(s,2H); ESMS calcd (C$_{25}$H$_{18}$ClN$_5$O$_2$): 454.11; found: 455.1 (M+H)$^+$.

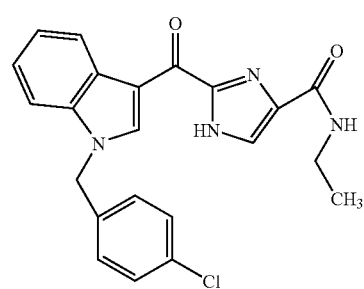

Compound 45

$^1$H NMR (CD$_3$OD) δ 9.57(s, 1H), 8.44(dd, 1H, J=6.3&1.8 Hz), 7.80 (s, 1H ), 7.36–7.17 (m, 9H), 5.59 (s, 2H), 3.45 (quart, 2H, J=7.2 Hz), 1.23 (t, 3H, J=7.2 Hz); ESMS calcd (C$_{22}$H$_{19}$ClN$_4$O$_2$): 406.12; found: 407.1 (M+H)$^+$.

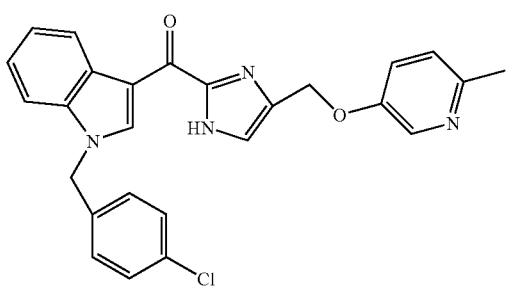

Compound 46

$^1$H NMR (CDCl$_3$): δ 9.22 (s, 1H), 8.55 (d, 1H, J=8.1 Hz), 8.16 (d, 1H, J=2.7 Hz), 7.70–7.03 (m, 11H), 5.35 (s, 2H), 4.73 (s, 2H), 2.46 (s, 3H); ESMS calcd (C$_{26}$H$_{21}$ClN$_4$O$_2$): 456.14; found: 457.1 (M+H)$^+$.

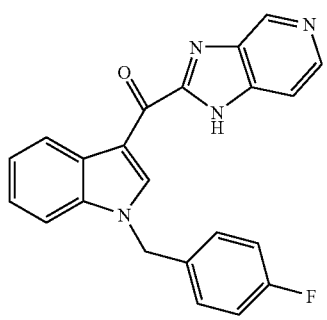

Compound 47

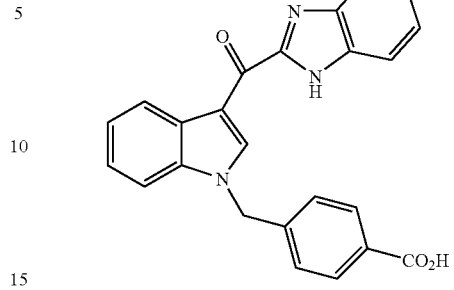

Compound 50

¹H NMR (DMSO-d₆) δ 5.82 (s, 2H), 7.32 (m, 2H), 7.49 (m, 4H), 7.82 (m, 2H ), 8.58 (m, 2H), 9.36 (1H), 9.59 (1H) ppm; ESMS calcd ($C_{22}H_{15}FN_4O$): 370; found: 371(M+H)⁺.

¹H NMR (DMSO-d₆) δ 5.64 (s, 2H), 7.19 (m, 2 H), 7.24 (m, 2H), 7.55 (m, 2H), 7.82 (m, 2H), 8.22 (m, 1H), 8.43 (m, 1H), 9.02 (s. 1H), 9.52 (s, 1H) ppm; ESMS calcd ($C_{20}H_{16}N_4O_3$): 396; found: 397 (M+H)⁺.

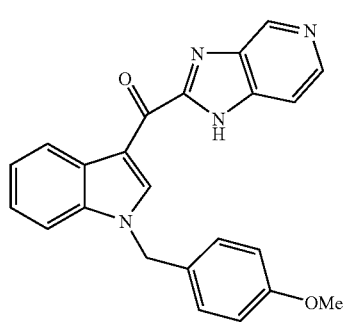

Compound 48

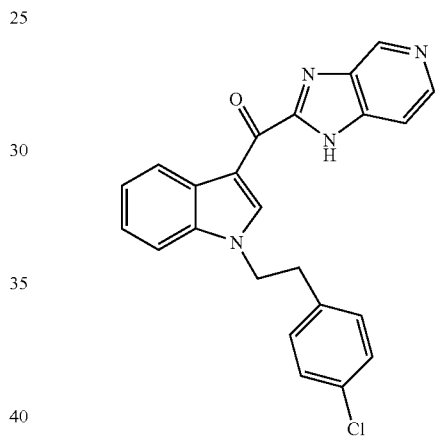

Compound 51

¹H NMR (DMSO-d₆) δ 3.68(s, 3H), 5.61 (s, 2H), 6.91 (m, 2 H), 7.28 (m, 4H ), 7.65 (m, 2H), 8.16 (m, 2H), 8.20 (m, 2H), 8.65 (m, 2H), 9.38 (s, 2H), 9.62 (s. 2H) ppm; ESMS calcd ($C_{20}H_{18}N_4O_2$): 382; found: 383 (M+H)⁺.

¹H NMR (DMSO-d₆) δ 3.18(t, 2H), 4.64 (t, 2H), 6.91 (m, 2 H), 7.28–7.78 (m, 8H), 8.44 (m, 2H), 9.20 (m, 2H) ppm; ESMS calcd ($C_{20}H_{17}ClN_4O$): 400; found: 401 (M+H)⁺.

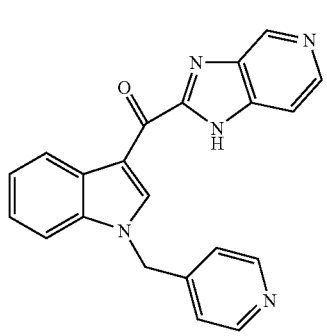

Compound 49

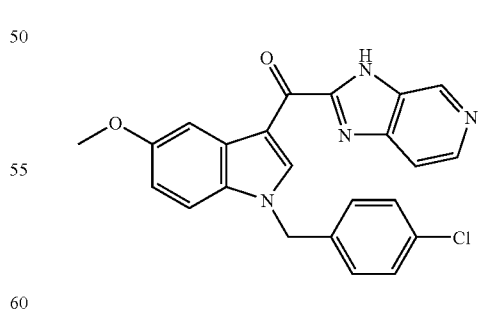

Compound 52

¹H NMR (DMSO-d₆) δ 5.80 (s. 2H), 7.19 (m, 2 H), 7.35 (m, 2H), 7.55 (m, 1H), 7.62 (m, 1H), 8.42 (m, 2H), 8.53 (m, 2H), 9.13 (s, 1H), 9.52 (s, 1H) ppm; ESMS calcd ($C_{21}H_{15}N_5O$): 353; found: 354 (M+H)⁺.

¹H NMR (DMSO-d₆) δ 3.82 (s, 3H), 5.70 (s, 2H), 6.90 (d, J=9.1 Hz, 1H), 7.3–7.4 (AB, J=7.8 Hz, 4H), 7.52 (d, J=9.1 Hz, 1H), 7.62 (d, J=3.5 Hz, 1H), 7.95 (s, 1 H), 8.38 (m, 1H), 9.08 (s, 1H), 9.44 (s, 1H) ppm; ESMS calcd ($C_{23}H_{17}ClN_4O_2$): 416.10; found: 417.1 (M+H)⁺.

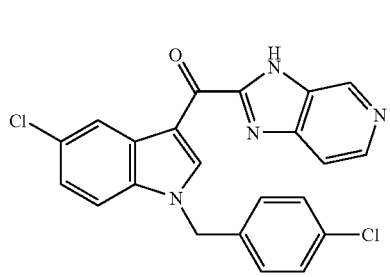

Compound 53

¹H NMR (DMSO-d₆) δ 5.75 (s, 2H), 7.25–7.45 (AB, J=7.8 Hz, 4 H), 7.30 (m, 1H), 8.42 (m, 2H), 9.12 (s, 1H), 9.55(s, 1H) ppm; ESMS calcd (C$_{22}$H$_{14}$C$_{12}$N$_4$O): 420.05; found: 421.0 (M+H)$^+$.

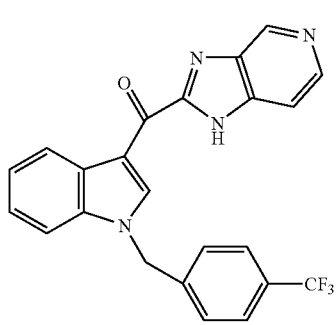

Compound 56

¹H NMR (DMSO-d₆) δ 5.83 (s, 2H), 7.36 (m, 2H), 7.62 (m, 4H), 7.81 (s, 1H ), 8.43 (m, 2H), 9.14 (s, 1H), 9.53 (s, 1H); ESMS Calcd (C$_{24}$H$_{16}$F$_3$N$_3$O): 419.12, found: 420.1 (M+H)$^+$.

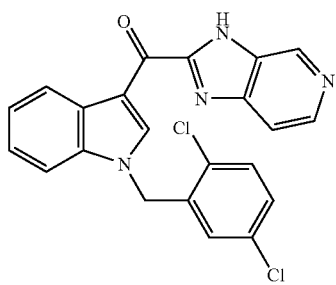

Compound 54

¹H NMR (DMSO-d₆) δ 5.80 (s, 2H), 7.03 (s, 1 H), 7.40 (m, 2H), 7.48 (m, 1H), 7.62 (m, 2H), 8.12 (m, 1H), 8.45 (m, 1H), 8.65 (m, 2H), 9.40 (s, 1H), 9.58 (s, 1H) ppm; ESMS calcd (C$_{22}$H$_{14}$C$_{12}$N$_4$O): 420.05; found: 421.0 (M+H)$^+$.

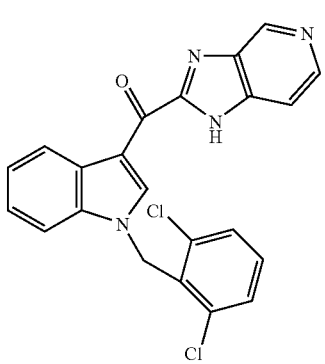

Compound 57

¹H NMR (DMSO-d₆) δ 5.85 (s, 2H), 7.40 (m, 2H), 7.59 (m, 2H), 7.80 (m, 5H ), 8.44 (m, 2H), 9.04 (s, 1H), 9.24 (s, 1H); ESMS calcd (C$_{23}$H$_{15}$Cl$_2$N$_3$O): 419.06; found: 420.0 (M+H)$^+$.

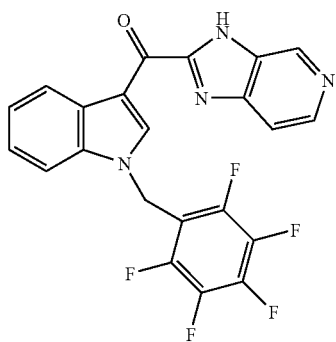

Compound 55

¹H NMR (DMSO-d₆) δ 5.94 (s, 2H), 7.45 (m, 2 H), 7.65 (d, J=9.1 Hz, 1H), 8.05 (m, 1H), 8.42 (d, J=9.1 Hz, 1H), 8.62 (d, J=7.5 Hz, 1H), 9.40 (s, 1H), 9.58 (s, 1H) ppm; ESMS calcd (C$_{22}$H$_{11}$F$_5$N$_4$O): 442.09; found: 443.1 (M+H)$^+$.

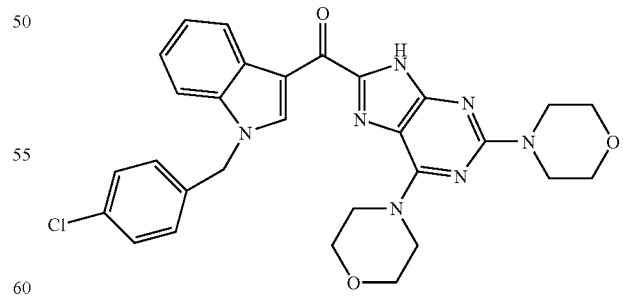

Compound 58

¹H NMR (DMSO-d₆) δ 3.6–3.9 (m, 12H), 4.1–4.3 (br, 4H), 5.6 (s, 2H), 7.3–7.5 (m, 6H), 7.7 (m, 1H), 8.4 (m, 1H), 9.0 (s, 1H). ESMS calcd for (C$_{29}$H$_{28}$ClN$_7$O$_3$): 557.1; found: 558.1 (M+H)$^+$.

Compound 59

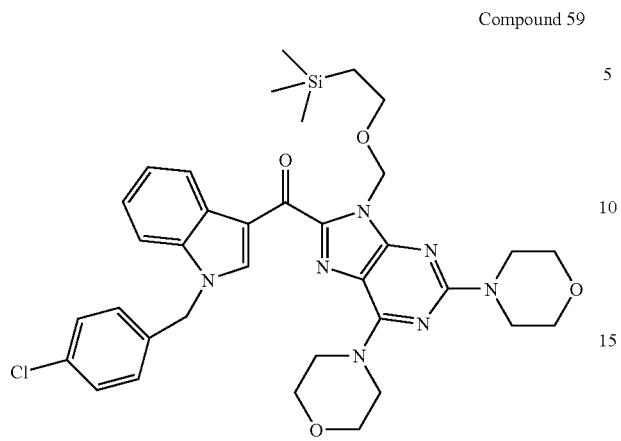

¹H NMR (CDCl₃) δ −0.9 (s, 9H), 0.95 (t, 2H, J=8), 3.65 (t, 2H, J=8), 3.7–3.85 (br, 12H), 4.23 (br, 4H), 5.35 (s, 2H), 6.00 (s, 2H), 7.12 (d, 2H, J=8), 7.25–7.40 (m, 5H), 8.51 (s, 1H), 8.60 (d, 1H, J=8). ESMS calcd for ($C_{35}H_{42}ClN_7O_4Si$): 687.3; found: 688.3 (M+H)⁺.

Compound 60

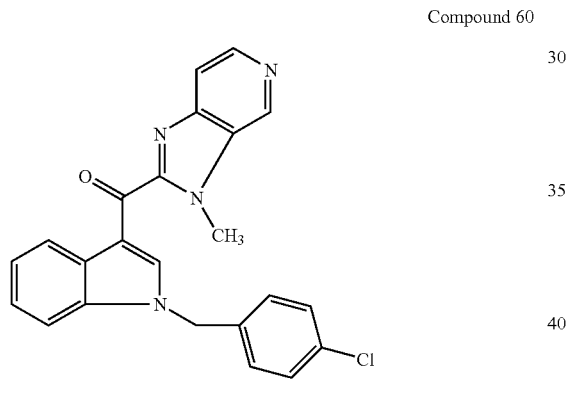

¹H NMR (CD₃OD) δ 9.08(s,1H), 8.67–8.62 (m, 4H), 8.29 (dd, 1H, J=1&6), 8.06 (d, 1H, J=6), 7.56–7.39 (m, 4H), 5.67 (s, 2H), 4.50 (s, 3H); ESMS calcd for ($C_{23}H_{18}ClN_4O$): 400.11; found: 401.1 (M+H)⁺.

Compound 61

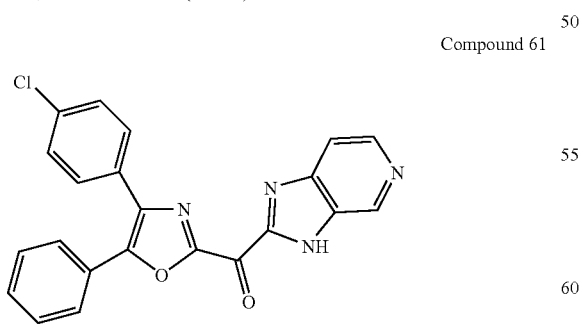

¹H NMR (DMSO-d₆) δ 7.34 (s, 1H), 7.62 (m, 5H), 7.83 (m, 5H), 8.74 (m, 1H ), 9.43 (s, 1H). ESMS calcd ($C_{22}H_{13}ClN_4O_2$): 400.1; found: 401.1 (M+H)⁺.

Compound 62

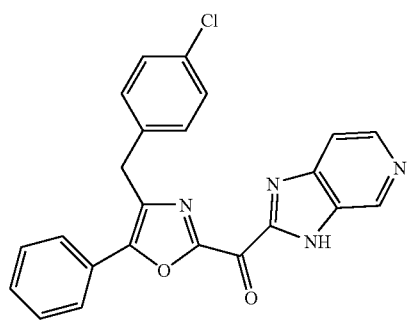

¹H NMR (DMSO-d₆) δ 4.31 (s, 2H), 7.40 (m, 9H), 7.73 (m, 2H), 8.57 (m, 1H ), 9.36 (s, 1H). ESMS calcd ($C_{23}H_{15}ClN_4O_2$): 414.1; found: 415.1 (M+H)⁺.

Compound 63

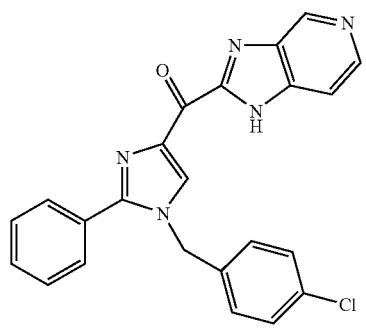

¹H NMR (CDCl₃ δ 5.31 (s, 1H), [5.76 (s, 1H)], [6.72 (d, 2H)], 7.06 (d, 2H), 7.35 (m, 2H), 7.55 (m,), 8.53 (m,) 9.46 s, 1H); ESMS Calcd ($C_{24}H_{17}ClN_4O$): 412.11, found 414.1 (M+H)⁺.

Compound 64

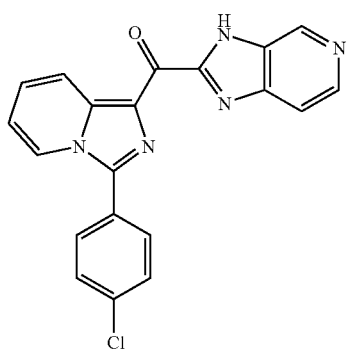

¹H NMR (CD₃OD) δ 7.18 (m, 1H), 7.58 (m, 1H), 7.62 (AB, J=8.1 Hz, 2 H), 7.80 (, 1H), 8.05(AB, J=8.1 Hz, 2H), 8.41(m, 1H), 8.62 (m, 2H), 9.06 (s, 1H) ppm; ESMS calcd ($C_{20}H_{12}ClN_5O$): 373.071; found: 374.1 (M+H)⁺.

Compound 65

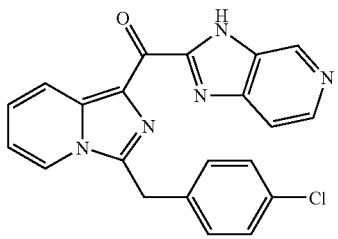

$^1$H NMR (DMSO-$d_6$) δ 4.58 (s, 2H), 7.06 (m, 1H), 7.35 (m, 4 H), 7.45 (m, 1H), 7.62 (m, 1H), 8.25–8.50 (m, 3H), 9.06 (s, 1H) ppm; ESMS calcd ($C_{21}H_{14}ClN_5O$): 387.09; found: 388.1 (M+H)$^+$.

Example 12

Compound (1) Demonstrates Anti-Cancer Activity (In Vitro)

The in vitro activity of the compounds was determined in the following seven human cancer cell lines. MDA435 (human breast cancer), MIP10 (human colon cancer), HL-60 (human myeloid leukemia), U937 (human leukemia), p388 (murine leukemia), DU-145 (human prostate cancer), MES-SA (human uterine sarcoma) were obtained from ATCC (American Type of Culture Collection).

The cell lines were maintained in RPMI1640(GIBCO) supplemented with 10% FCS, 100 units/ml penicillin, 100 ug/ml streptomycin, and 2 mM L-glutamine. The cells were split every third day and diluted to a concentration of 2×10$^5$ cells/ml one day before experiment. All experiments were performed on exponentially growing cell culture. Cell densities were 2.5×104 cells/ml in all experiment.

A stock solution of Compound (1) was prepared by dissolving the compound at a concentration of 1 mM in 100% DMSO. Final concentrations were obtained by diluting the stock solution directly into the tissue culture medium. Cells were incubated with varying concentrations of the compounds for 72 hours and the IC$_{50}$ was determined by MTS (i.e. 3-(4.5.-dimethylthiazol-2-yl)-2.5-diphenyl tetrazolium bromide) assay. IC$_{50}$ stands for the concentration of compound required to inhibit 50% tumor cell growth. The results are shown in Table 1.

TABLE 1

In Vitro Anti-Cancer Activity of Compound (1) and Taxol (positive control)

| Cancer Cell Lines | IC$_{50}$ (uM) |
|---|---|
| MDA-435 | 0.05 |
| HL-60 | 0.05 |
| p388 | 0.05 |
| DU-145 | 0.05 |
| MES-SA | 0.01 |
| H2 | 0.05 |
| A549 | 0.05 |

As can be seen from the data in Table 1, Compound (1) demonstrated significantly high anti-cancer activity (IC$_{50}$: 0.01–0.05 uM) against seven cancer cell lines with a wide variety of cancer cell types.

Example 13

Compound (1) Has Anti-Cancer Activity Against Multi-Drug Resistant Cancer Cells In Vitro In vitro activity was determined in two MDR (Multi Drug Resistant) human cancer cell lines. HL-60/TX1000 was isolated in vitro by subculturing HL-60 in progressively higher concentration of Taxol. HL-60/TX1000 cells overexpress mdr-1 mRNA and p-glycoprotein, as determined by western blot and immunofluorescence labeling with antiPGP antibodies. The cell is cross-resistant to Taxol, Vincristine, Adriamycin, Etoposide and Doxorubicin. MES-SA/Dx5 was established in the presence of increasing concentrations of Doxorubicin. The cells express high levels of mdr-1 mRNA and p-glycoprotein and exhibit cross resistance to more than fifteen chemotherapeutic agents including Taxol, Etoposide, Mitomycin C, Colchicine, Vinblastine, Dactinomycin, 5-Fluorouracil and Methotrexate. MES-SA/Dx5 was purchased from ATCC.

The procedure for culturing the cells and assaying cancer cell growth inhibition were as described in Example 12. The results are shown in Table 2.

TABLE 2

In Vitro Anti-Cancer Activity of Compound (1), Taxol (control) and Vincristine (control) Against Multi Drug Resistance Cancer Cell Lines

| Cancer Cell Lines | IC$_{50}$ (uM) | | |
|---|---|---|---|
| | Compound (1) | Taxol | Vincristine |
| HL-60/TX1000 | 0.05 | 5 | 5 |
| MES-SA/DX-5 | 0.05 | 5 | 1 |

The data in Table 2 shows Taxol and Vincristine were not effective (IC$_{50}$: 1–5 uM) against the MDR cell lines (MES-SA/DX5, HL-60/TX1000). On the other hand, Compound (1) showed high anti-cancer activity against these MDR cancer cell lines.

Example 14

Compound (2) Demonstrates Anti-Cancer Efficacy on Human Breast Tumor (MDA435) Xenograft Model (In Vivo)

The in vivo anti-cancer efficacy of Compound (2) was assessed in tumor bearing mice using a tumor growth inhibition assay. Human breast tumor (MDA-435) cells were implanted by injection of a tumor cell suspension subcutaneously in the flank of a nude mouse. Treatment of the tumor with an experimental compound began after the tumor had been established (volume was approximately 100 mm$^3$). The animal then began a multiple injection schedule where the compound was administered orally. Tumors were measured two times a week. During the course of this assay, animals were monitored daily for signs of toxicity including body weight loss.

A supplemented media was prepared from 50% DMEM/ Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate, 1% MEM Non-Essential Amino Acids. FBS was obtained from Sigma Chemical Co. and other ingredients were obtained from Invitrogen Life Technologies, USA). The supplemental media was warmed to 37° C. and 50 ml of media was added to a 175 cm² tissue culture flask.

The cells used in the assay were MDA435 Human Breast Carcinoma from the American Type Culture Collection. One vial of MDA-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm² tissue culture flask containing supplemented media. The cells were incubated overnight and the media was removed and replaced with fresh supplemented media the next day. The flask was incubated until the flask became about 90% confluent. This typically took about 5–7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2–3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1–3 million cells/flask were seeded into 5–7 tissue culture flasks (175 cm²). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MDA-435, 100 million cells were suspended with 2.0 ml of sterile PBS to a final concentration of 50 million cells/ml in order to inject 5 million cells in 0.1 ml/mouse.

Mice (CD-1 nu/nu) were obtained from Charles River Laboratories: nomenclature: Crl:CD-1-nuBR, Age: 6–8 weeks. The mice were allowed to acclimate for 1 week prior to their being used in an experimental procedure.

Implantation of the MDA-435 tumor cell suspension took place into the corpus adiposum of the female CD-1 nu/nu mouse. This fat body is located in the ventral abdominal viscera of the mouse. Tumor cells were implanted subsutaneously into the fat body located in the right quadrant of the abdomen at the juncture of the os coxae (pelvic bone) and the os femoris (femur). 5 million MDA-435 cells in 0.1 ml of sterile PBS were injected using 27 G (½ inch) needle. MDA-435 tumors developed 2–3 weeks after implantation.

A dosing solution for compound administration was prepared by dissolving 1 gram of Compound (2) in 10 ml of acetone (HPLC grade), and sonicated for 5 minutes using 550 Sonic Dismembrator. 1.2 equivalents of 1 N HCl aqueous solution were added to the acetone solution which was then sonicated for 5 minutes. All solvent was then evaporated from the solution by using Speed Vac Plus SC 250 DDA over night. The dried powder was used for preparing the dosing solution of Compound (2). 1% Methyl cellulose (MC) vehicle was prepared by dissolving 1.0 gram of Methyl cellulose, 400 cps, U.S.P. (Spectrum Laboratory Products, Cat. # ME136) in 100 mL of H₂O. This mixture was then stirred for 12 hours at room temperature to produce a clear 1% MC solution. After autoclaving the solution for 15 minutes at 120° C., the 1% MC solution was allowed to stand at room temperature for 3 hours prior to being used for formulating orally administered compounds. Compound (2) was prepared in 1% MC and orally administered to the mice through a standard gavage tube attached to a hypodermic syringe. This method permits a direct placement of the compound into the stomach. The dosing volume for the mice was 10 mL/kg.

1% MC Dosing Solution of the Compound (2) was injected orally into the mice bearing MDA435 human breast tumor according to the following protocol:

| Group | Compounds | Dose |
|---|---|---|
| 1 | Vehicle | |
| 2 | Compound (2) | 25 mg/kg |

Dosing schedule: 3 times a week (Monday, Wednesday, Friday) for 3 weeks; 5 mice were used for each group FIG. 1 shows the oral anti-tumor efficacy of Compound (2). As can be seen from FIG. 1, Compound (2) significantly inhibits tumor growth of MDA435 in nude mice at 25 mg/kg in a dose dependent manner in nude mice bearing MDA435 human breast tumor. No significant loss of weight was observed (less than 5%), indicating minimal side effects.

Example 15

Compounds (2)–(12) Demonstrates High Anti-Cancer Activity Against the Multi-Drug Resistant MES-SA/DX5 and HL-60/TX1000 Cell Lines (In Vitro)

The protocol described in Examples 12–13 was used to assay inhibition by Compound (2)–(12) on the growth of the multidrug resistant cancer cell line MES-SA/DX5 and HL-60/TX1000. The results are shown in Table 3.

TABLE 3

In Vitro Anti-Cancer Activity of Compound (2)–(12) against Multi Drug Resistant Cell Lines MES-SA/DX5 and HL-60/TX1000

| Compound | $IC_{50}$ (uM) MES-SA/DX5 | $IC_{50}$ (uM) HL-60/TX1000 |
|---|---|---|
| Compound 2 | 0.05 | 0.05 |
| Compound 3 | 0.05 | 0.04 |
| Compound 4 | 0.05 | 0.05 |
| Compound 5 | 0.5 | 0.1 |
| Compound 6 | 0.05 | 0.05 |
| Compound 7 | 0.5 | 0.05 |
| Compound 8 | 0.1 | 0.05 |
| Compound 9 | 0.5 | 0.5 |
| Compound 10 | 0.5 | 0.5 |
| Compound 11 | 0.5 | 0.5 |
| Compound 12 | 0.5 | 0.5 |

The data in Table 3 shows that Compounds (2)–(12) demonstrated significant anti-cancer activity ($IC_{50}$: 0.04–0.5uM) against MES-SA/DX5 and HL60/TX1000, while Taxol showed very weak anti-cancer activity (IC50: 5 uM) against the multi-drug resistant cell lines.

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition comprising a pharmaceutically acceptable carrier or diluent and a compound represented by the following structural formula:

or a pharmaceutically acceptable salt thereof, wherein:

$R_1$ is a substituted or unsubstituted 2-imidazolyl group which is optionally fused to a substituted or unsubstituted aryl group;

$Z_1$ is =O, =S, =N—$OR_{11}$ or =$NR_{11}$;

R is represented by a structural formula selected from:

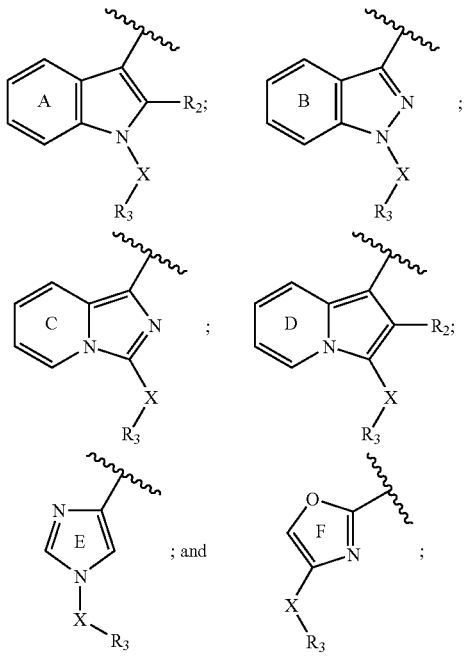

Rings A–F are independently substituted or unsubstituted and are optionally fused to an aryl group;

$R_2$ is —H, a substituted or unsubstituted alkyl group or a substituted or unsubstituted aryl group;

$R_3$ is a substituted or unsubstituted aryl group or a substituted or unsubstituted aliphatic group;

X is a covalent bond, —C($R_4R_5$)—, —N($R_4$)—, —O—, —S—, —S(O)—, —S(O)$_2$—, —C(=O)—, —C(=O)—N($R_4$)— or —N($R_4$)—C(=O)—;

$R_4$ and $R_5$ are independently —H, an aliphatic group or a substituted aliphatic group; and $R_{11}$ is —H or a substituted or unsubstituted alkyl group; provided that when R is represented by

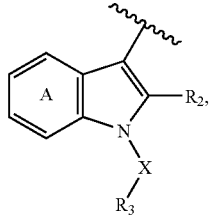

then X is not —S(O)— or —S(O)$_2$— and $R_3$ is not an aliphatic or substituted aliphatic group.

2. The pharmaceutical composition of claim 1 wherein X is a covalent bond, —C($R_4R_5$)—, —N($R_4$)—, —O—, C(=O)—, —C(=O)—N($R_4$)— or —N($R_4$)—C(=O)— and $R_3$ is a substituted or unsubstituted aryl group.

3. The pharmaceutical composition of claim 2 wherein R is represented by a structural formula selected from:

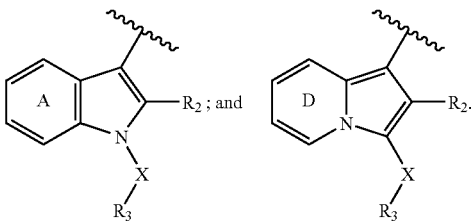

4. The pharmaceutical composition of claim 3 wherein Rings A–F are a substituted or unsubstituted phenyl group; $R_2$ is —H; $Z_1$ is =O; and X is —C($R_4R_5$)—, —N($R_4$)— or —O—.

5. The pharmaceutical composition of claim 4 wherein X is —C($R_4R_5$)—.

6. The pharmaceutical composition of claim 5 wherein $R_1$ is represented by the following structural formula:

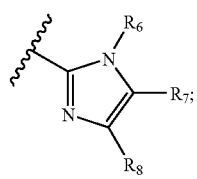

wherein:

$R_6$ is —H, an unsubstituted aliphatic group or a substituted aliphatic group, —C(O)$R^g$, —S(O)$_2$—$R^g$ or —S(O)$_2$—N($R^g$)$_2$;

$R_7$ and $R_8$ are independently —H, —OH, —Br, —Cl, —F, —$OR^a$, —O—$COR^a$, —$COR^a$, —CN, —NO$_2$, —COOH, —SO$_3$H, —NH$_2$, —$NHR^a$, —N($R^aR^b$), —$COOR^a$, —CHO, —CONH$_2$, —$CONHR^a$, —CON($R^aR^b$), —$NHCOR^a$, —$NRCOR^a$, —NHCONH$_2$, —$NHCONR^aH$, —NHCON($R^aR^b$), —$NR^cCONH_2$, —$NR^cCONR^aH$, —$NR^cCON(R^aR^b)$, —C(=NH)—NH$_2$, —C(=NH)—$NHR^a$, —C(=NH)—N($R^aR^b$), —C(=$NR^c$)—NH$_2$, —C(=$NR^c$)—$NHR^a$, —C(=$NR^c$)—N($R^aR^b$), —NH—C(=NH)—NH$_2$, —NH—C(=NH)—$NHR^a$, —NH—C(=NH)—N($R^aR^b$), —NH—C(=$NR^c$)—NH$_2$, —NH—C(=$NR^c$)—$NHR^a$, —NH—C(=$NR^c$)—N($R^aR^b$), —$NR^dH$—C(=NH)—NH$_2$, —$NR^d$—C(=NH)—$NHR^a$, —$NR^d$—C(=NH)—N($R^aR^b$), —$NR^d$—C(=$NR^c$)—NH$_2$, —$NR^d$—C(=$NR^c$)—$NHR^a$, —$NR^d$—C(=$NR^c$)—N($R^aR^b$), —NHNH$_2$, —$NHNHR^a$, —$NHR^aR^b$, —SO$_2$NH$_2$, —SO$_2NHR^a$, —SO$_2NR^aR^b$, —CH=$CHR^a$, —CH=$CR^aR^b$, —$CR^c$=$CR^aR^b$,—$CR^c$=$CHR^a$, —$CR^c$=$CR^aR^b$, —$CCR^a$, —SH, —$SR^a$, —S(O)$R^a$, —S(O)$_2R^a$, alkyl groups, substituted alkyl group, non-aromatic heterocyclic group, substituted non-aromatic heterocyclic group, benzyl group, substituted benzyl group, aryl group or substituted aryl group;

R$^a$–R$^d$ are each independently an alkyl group, substituted alkyl group, benzyl, substituted benzyl, aryl or substituted aryl group, or, —N(R$^a$R$^b$), taken together, can also form a substituted or unsubstituted non-aromatic heterocyclic group; and R$^g$ is —H or a substituted or unsubstituted aliphatic group.

7. The pharmaceutical composition of claim 6 wherein:

R$_6$ is —H, C1–C4 alkyl, C1–C4 hydroxyalkyl, —(C1–C4 alkylene)-O—(C1–C4 alkylene)-tri(C1–C4 alkyl)silane, —S(O)$_2$N(C1–C4 alkyl)$_2$, —S(O)$_2$NH(C1–C4 alkyl) or —S(O)$_2$NH$_2$;

R$_7$ and R$_8$ are independently —H, C1–C4 alkyl, C1–C4 hydroxylalkyl, (C1–C4 alkyl)$_3$-Si—O—(C1–C4 alkylene), pyridyl, C1–C4 alkyl substituted with pyridyl, C1–C4 alkyl substituted with —NH-pyridyl, C1–C4 hydroxyalkyl substituted with —NH-pyridyl, C1–C4 hydroxyalkyl substituted with -pyridyl, —S(O)$_2$-(phenyl), —S(O)$_2$-(tolulyl),

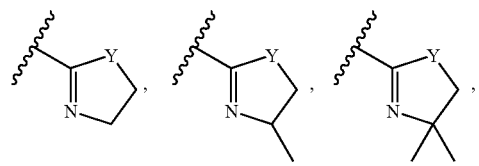

—C(O)-pyridyl, indolyl, —(C1–C4 alkylene)-O—(C1–C4 alkyl), C1–C4 alkyl substituted with —O-pyridyl, —CHO, —C(O)—O—(C1–C4 alkyl), —C(O)—NH—(C1–C4 alkyl), —C(O)—(C1–C4 alkylene)-pyridyl, oxazolinyl, —C(O)—(C1–C4 alkyl), —C=N—NH-phenyl, —C(O)—NH-pyridyl, —C(O)—NH-phenyl, —C=N—NH—(C1–C4 alkyl), —C=N—N—(C1–C4 alkyl)$_2$, —C(O)—NH—(C1–C4 alkyl), —C(O)—N—(C1–C4 alkyl)$_2$, —C(O)—(N-morpholino), —C(O)-imidazolyl, —C(O)—NH—(C1–C4 haloalkyl), —C(O)—N—(C1–C4 haloalkyl)$_2$, —CH$_2$—N$_3$, C1–C4 alkyl substituted with imidazolyl, —C1–C4 alkylene-NHC(O)—(C1–C4 alkyl), —C1–C4 alkylene-NHC(O)-(phenyl), —(C1–C4 alkylene)-NHC(O)-(tolulyl), —C1–C4-alkylene-NHC(O)-(methoxy, dimethoxy or trimethoxyphenyl); and Y is —S—, —O— or —N(H or C1–C4 alkyl or substituted alkyl)-.

8. The pharmaceutical composition of claim 7 wherein R$_4$ and R$_5$ are both —H; and R$_3$ is a substituted or unsubstituted phenyl or pyridyl group.

9. The pharmaceutical composition of claim 8 wherein Rings A and D are unsubstituted or substituted with one or more groups selected from —F, —Cl, —Br, —C1–C4 alkyl, C1–C4 alkoxy, —C1–C4 haloalkyl, C1–C4 haloalkoxy, —CN and —NH$_2$.

10. The pharmaceutical composition of claim 9 wherein R is represented by the following structural formula:

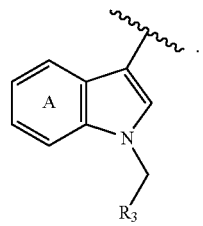

11. The pharmaceutical composition of claim 10 wherein:

R$_3$ is a phenyl or pyridyl group substituted with zero, one or more groups selected from —Br, —Cl, —F, —R$^e$, —OR$^e$, —CN, —COOR$^e$, —N(R$^e$)$_2$, —CON(R$^e$)$_2$, —NR$^e$COR$^f$, —NHCONH$_2$ and —SO$_2$N(R$^e$)$_2$; and each R$^e$ and R$^f$ are independently selected from —H, alkyl, and substituted alkyl.

12. The pharmaceutical composition of claim 11 wherein R$_3$ is a phenyl group substituted with zero, one or more groups selected from —Cl, —F, —R$^e$, —OR$^e$, —CN, —NH$_2$, —CONH$_2$, and —NHCOR$^f$.

13. The pharmaceutical composition of claim 12 wherein R$_3$ is a phenyl group substituted with zero, one or more groups selected from —CH$_3$, —CH$_2$CH$_3$, —F, —Cl, —CN and —OCH$_3$.

14. The pharmaceutical composition of claim 13 wherein R$_3$ is an unsubstituted phenyl group or a phenyl group monosubstituted with —CH$_3$, —CH$_2$CH$_3$, —F, —Cl, —CN or —OCH$_3$, wherein the phenyl group substituent is at the para position.

15. The pharmaceutical composition of claim 14 wherein R$_1$ is represented by the following structural formula:

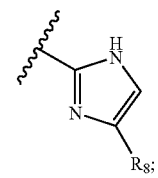

wherein R$_8$ is —C(O)NH$_2$, —C(O)CH$_3$, —C(O)CH$_2$CH$_3$, 2-pyridyl, —C(O)OCH$_3$, —C(O)OCH$_2$CH$_3$,

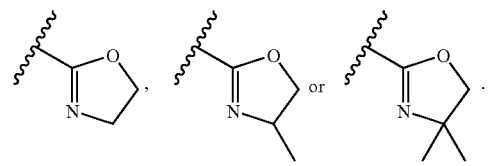

16. The pharmaceutical composition of claim 15 wherein Ring A is unsubstituted.

17. The pharmaceutical composition of claim 9 wherein R is represented by the following structural formula:

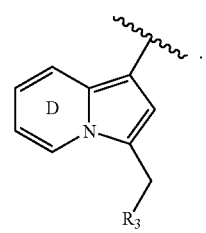

18. The pharmaceutical composition of claim 17 wherein:

R$_3$ is a phenyl or pyridyl group substituted with zero, one or more groups selected from —Br, —Cl, —F, —R$^e$,— OR$^e$, —CN, —COOR$^e$, —N(R$^e$)$_2$, —CON(R$^e$)$_2$, —NR$^e$COR$^f$, —NHCONH$_2$ and —SO$_2$N(R$^e$)$_2$; and each R$^e$ and R$^f$ is independently selected from —H, alkyl and substituted alkyl.

19. The pharmaceutical composition of claim 18 wherein R₃ is a phenyl group substituted with zero, one or more groups selected from —Cl, —F, —Rᵉ, —ORᵉ, —CN, —NH₂, —CONH₂ and —NHCORᶠ.

20. The pharmaceutical composition of claim 19 wherein R₃ is a phenyl group substituted with zero, one, or more groups selected from —CH₃, —CH₂CH₃, —F, —Cl, —CN and —OCH₃.

21. The pharmaceutical composition of claim 20 wherein R₃ is an unsubstituted phenyl group or a phenyl group monosubstituted with —CH₃, —CH₂CH₃, —F, —Cl, —CN or —OCH₃, wherein the phenyl group substituent is at the para position.

22. The pharmaceutical composition of claim 21 wherein R₁ is represented by the following structural formula:

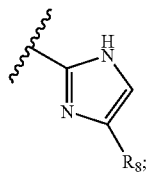

wherein R₈ is —C(O)NH₂, —C(O)CH₃, —C(O)CH₂CH₃, 2-pyridyl, —C(O)OCH₃, —C(O)OCH₂CH₃,

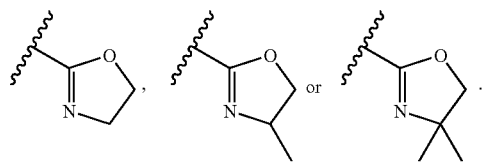

23. The pharmaceutical composition of claim 22 wherein Ring D is unsubstituted.

24. The pharmaceutical composition of claim 1 wherein R₁ is represented by the following structural formula:

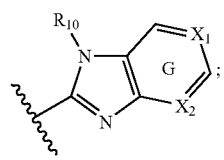

wherein:
R₁₀ is —H, an unsubstituted aliphatic group or a substituted aliphatic group, —C(O)—Rᵍ, —S(O)₂—Rᵍ, or —S(O)₂—N(Rᵍ)₂;
X₁ and X₂ are independently —CH— or —N—;
Ring G is substituted or unsubstituted; and
each Rᵍ is —H or a substituted or unsubstituted aliphatic group.

25. A pharmaceutical composition represented by the following structural formula:

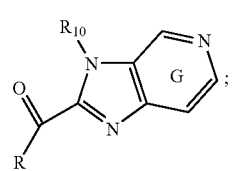

or a pharmaceutically acceptable salt thereof, wherein:
Ring G is substituted or unsubstituted;
R₁₀ is —H or a C1–C4 alkyl group;
R is represented by a structural formula selected from:

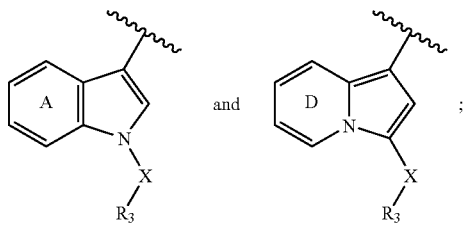

wherein Rings A and D are substituted or unsubstituted; X is —C(R₄R₅)—, —O— or —NR₄—; and R₃ is a substituted or unsubstituted phenyl or pyridyl group.

26. The pharmaceutical composition of claim 25 wherein X is —C(R₄R₅)—.

27. The pharmaceutical composition of claim 26 wherein X is —CH₂— and Ring G is unsubstituted.

28. The pharmaceutical composition of claim 25 wherein:
Rings A and D are unsubstituted or substituted with one or more substituents selected from —F, —Cl, —Br, —C1–C4 alkyl, C1–C4 alkoxy, —C1–C4 haloalkyl, C1–C4 haloalkoxy, —CN and —NH₂;
R₃ is a phenyl or pyridyl group substituted with zero, one or more groups selected from —Br, —Cl, —F, —Rᵉ, —ORᵉ, —CN, —COORᵉ, —N(Rᵉ)₂, —CON(Rᵉ)₂, —NRᵉCORᶠ, —NHCONH₂ and —SO₂N(Rᵉ)₂; and
each Rᵉ and Rᶠ is independently selected from —H, alkyl, and substituted alkyl.

29. The pharmaceutical composition of claim 28 wherein R₃ is a phenyl group substituted with zero, one, or more groups selected from —Cl, —F, —Rᵉ, —ORᵉ, —CN, —NH₂, —CONH₂, and —NHCORᶠ.

30. The pharmaceutical composition of claim 29 wherein R₃ is a phenyl group substituted with zero, one or more groups selected from —CH₃, —CH₂CH₃, —OCH₃, —CN, —F, and —Cl.

31. A pharmaceutical composition represented by the following structural formula:

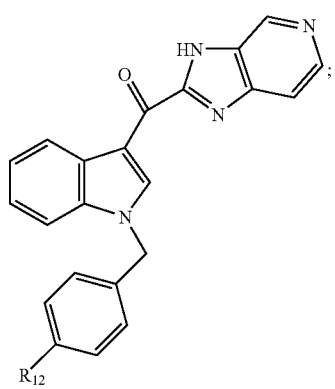

or a pharmaceutically acceptable salt thereof, wherein R₁₂ is —CH₃, —CH₂CH₃, —OCH₃, —CN, —F, or —Cl.

32. A pharmaceutical composition represented by the following structural formula:

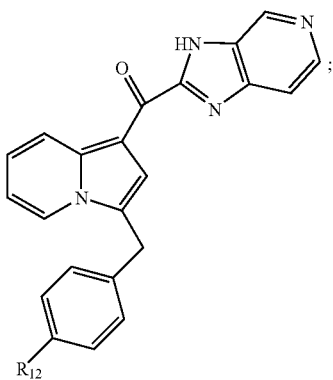

or a pharmaceutically acceptable salt thereof, wherein $R_{12}$ is —$CH_3$, —$CH_2CH_3$, —$OCH_3$, —CN, —F or —Cl.

33. A pharmaceutical composition represented by the following structural formula:

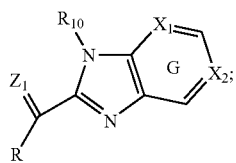

or a pharmaceutically acceptable salt thereof, wherein:

$Z_1$ is =O, =S, =$NOR_{11}$ or =$NR_{11}$

R is represented by a structural formula selected from:

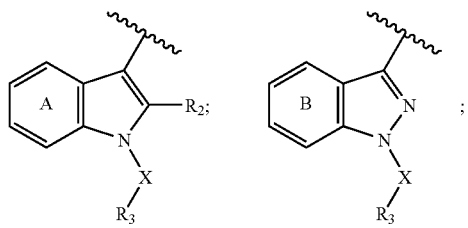

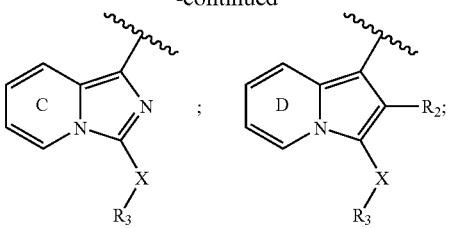

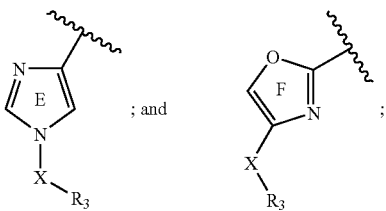

Rings A–F are independently substituted or unsubstituted and are optionally fused to an aryl group;

$R_2$ is —H or a substituted or unsubstituted alkyl group;

$R_3$ is a substituted or unsubstituted aryl group or a substituted or unsubstituted aliphatic group;

X is a covalent bond, —C($R_4R_5$)—, —N($R_4$)—, —O—, —S—, —S(O)—, —S(O)$_2$—, —C(=O)—, —C(=O)—N($R_4$)— or —N($R_4$)—C(=O)—;

$R_4$ and $R_5$ are independently —H, an aliphatic group or a substituted aliphatic group;

$R_{10}$ is —H, an unsubstituted aliphatic group or a substituted aliphatic group, —C(O)—$R^g$, —S(O)$_2$—$R^g$, or —S(O)$_2$—N($R^g$)$_2$;

$R_{11}$ is —H or a substituted or unsubstituted alkyl group;

$X_1$ and $X_2$ are independently —CH— or —N—;

Ring G is substituted or unsubstituted; and each $R^g$ is —H or a substituted or unsubstituted aliphatic group.

* * * * *